United States Patent
Wykes

(10) Patent No.: US 12,429,477 B2
(45) Date of Patent: Sep. 30, 2025

(54) METHODS AND AGENTS FOR DETERMINING PATIENT STATUS

(71) Applicant: The Council of the Queensland Institute of Medical Research, Herston (AU)

(72) Inventor: Michelle Wykes, Herston (AU)

(73) Assignee: The Council of the Queensland Institute of Medical Research, Hearston (AU)

( * ) Notice: Subject to any disclaimer, the term of this patent is extended or adjusted under 35 U.S.C. 154(b) by 853 days.

(21) Appl. No.: 17/639,815

(22) PCT Filed: Sep. 3, 2020

(86) PCT No.: PCT/AU2020/050921
§ 371 (c)(1),
(2) Date: Mar. 2, 2022

(87) PCT Pub. No.: WO2021/042163
PCT Pub. Date: Mar. 11, 2021

(65) Prior Publication Data
US 2022/0326226 A1    Oct. 13, 2022

(30) Foreign Application Priority Data
Sep. 3, 2019   (AU) .............................. 2019903243

(51) Int. Cl.
*G01N 33/50*    (2006.01)
*G01N 33/574*   (2006.01)

(52) U.S. Cl.
CPC ....... *G01N 33/5091* (2013.01); *G01N 33/574* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 2007/0190127 A1* | 8/2007 | Zhou ..................... | A61P 9/04 424/490 |
| 2008/0145358 A1* | 6/2008 | Zabludoff ............... | A61P 35/00 435/7.1 |
| 2008/0248506 A1* | 10/2008 | Bass ..................... | G01N 33/6875 435/7.92 |
| 2010/0041069 A1* | 2/2010 | Lederkremer ........... | G01N 33/68 435/7.1 |
| 2011/0129458 A1* | 6/2011 | Dolk ..................... | H04L 47/50 435/69.6 |
| 2015/0197571 A1* | 7/2015 | Freeman ................. | A61P 1/04 435/69.6 |

FOREIGN PATENT DOCUMENTS

| WO | WO 2018/027252 | 2/2018 |
| WO | WO 2018/027281 | 2/2018 |
| WO | WO2018/045422 | 3/2018 |
| WO | WO 2019/104381 | 6/2019 |
| WO | WO 2019/136531 | 7/2019 |

OTHER PUBLICATIONS

Yang (Oncology Letters 2018 vol. 15:2743-2748 (Year: 2018).*
Menezes Trends in Parasitology 2023 39:682-695 (Year: 2023).*
Xiao J. Exp. Med. 2014 vol. 211:943-959 (Year: 2014).*
Li (Cancer Science 2018 vol. 109:2435-2445 (Year: 2018).*
Blackburn, S. D. et al "Tissue-Specific Differences in PD-1 and PD-L1 Expression during Chronic Viral Infection: Implications for CD8 T-Cell Exhaustion". Journal of Virology, vol. 84, No. 4, p. 2078-2089. Feb. 2010.
Liang, S. C. et al "Regulation of PD-1, PD-L1 and PD-L2 expression during normal and autoimmune responses". European Journal of Immunology, vol. 33(10), p. 27062716. 2003.
Solinas, C. et al "Immune Checkpoint Molecules on Tumor-Infiltrating Lymphocytes and Their Association with Tertiary Lymphoid Structures in Human Breast Cancer". Frontiers in Immunology, vol. 8, Article 1412, p. 1-16. Oct. 2017.

* cited by examiner

*Primary Examiner* — Changhwa J Cheu
(74) *Attorney, Agent, or Firm* — Casimir Jones, S.C.; Mary Ann D. Brow

(57) ABSTRACT

Disclosed are methods and agents for predicting response to therapy, immune status and/or disease progression. More particularly, disclosed are methods, agents and kits for analyzing cellular distribution of PD-L2, including its nuclear localization, for stratifying a patient as a likely responder or non-responder to a therapy, for predicting treatment outcome of a patient with a therapy, for managing treatment of a patient with a therapy, for monitoring a disease in a patient following treatment with a therapy, for determining the status of a disease and/or for determining the immune status of a patient.

11 Claims, 12 Drawing Sheets

(A)

(B)

(C)

(D)

(E)

(F)

(A)

(B)

(C)

(A)

(B)

(A)  Day 15 tumors (B)  Day 21 tumors (A)

(B)

(A)

(B)

METHODS AND AGENTS FOR DETERMINING PATIENT STATUS

RELATED APPLICATIONS

This application claims priority to Australian Provisional Application No. 2019903243 entitled "Methods and Agents for Determining Patient Status", filed on 3 Sep. 2019, the entire content of which is hereby incorporated herein by reference in its entirety.

TECHNICAL FIELD

This disclosure relates generally to methods and agents for predicting response to therapy, immune status and/or disease progression. More particularly, the present disclosure relates to methods, agents and kits for analyzing cellular distribution of PD-L2, including its nuclear localization, for stratifying a patient as a likely responder or non-responder to a therapy, for predicting treatment outcome of a patient with a therapy, for managing treatment of a patient with a therapy, for monitoring a disease in a patient following treatment with a therapy, for determining the status of a disease and/or for determining the immune status of a patient.

Various bibliographic references referred to by number in the specification are listed at the end of the description.

BACKGROUND

Dendritic cells (DCs) resident in tissues are crucial for surveillance of pathogens and cancer cells. These innate immune cells recognise pathogens and cancer-specific molecules to initiate immunity via several immune cell types (e.g., T-cells). DCs then balance immune activation, which controls disease, with immune suppression to minimize tissue damage by inflammation. It is now evident that some pathogens and cancer cells can commandeer immune suppressive mechanisms to subvert immunity and promote disease. An important immune suppressive mechanism is the interaction between programmed cell death-1 ligand 1 (PD-L1) on DCs and tumor cells with programmed cell death-1 (PD-1) on T-cells.

PD-L2, the second ligand for PD-1 has dual roles in immunity. While several studies showed a suppressive role for PD-L2 in T-cell responses (Latchman et al., 2001. *Nat Immunol* 2: 261-268; Brown et al., 2003. *J Immunol* 170: 1257-1266; Cai et al., 2004. *Cell Immunol* 230: 89-98; Xiao et al., 2014. *J Exp Med* 211: 943-959), others have shown that PD-L2 expressed on DCs enhances immunity (Liu et al., 2003. *J Exp Med* 197: 1721-1730; Shin et al., 2003. *J Exp Med* 198: 31-38) by inhibition of PD-1/PD-L1-mediated loss of T-cell function (Karunarathne. et al., 2016. *Immunity* 45: 333-345). Furthermore, reverse signaling via PD-L1 and/or PD-L2 into DC, leads to reduced DC maturation (Kuipers et al., 2006. *Eur J Immunol* 36: 2472-2482).

While investigating contribution of PD-1 ligands to malarial immunity, it was found that higher PD-L2 expression on blood dendritic cells, from *Plasmodium falciparum*-infected individuals, correlated with lower parasitemia (Karunarathne. et al., 2016, supra). Mechanistic studies in mice showed that PD-L2 was indispensable for establishing effective CD4$^+$ T-cell immunity against malaria, as it not only inhibited PD-L1 to PD-1 activity but also increased CD3 and inducible co-stimulator (ICOS) expression on T-cells. Furthermore, a comparison of DCs from mice with lethal and non-lethal malaria clearly showed the latter had higher PD-L2 levels but DCs from both groups had equivalent amounts of PD-L1 and PD-L2 mRNA.

SUMMARY

The present disclosure is based in part on the finding that increased translocation of PD-L2 to the nucleus of cells, including antigen-presenting cells (e.g., DC), immune effector cells (e.g., B-cells and T-cells) and tumor cells, correlates with increased severity of disease (e.g., diseases relating to pathogenic infections and cancer) decreased immunity (e.g., immune dysfunction including T-cell dysfunction such as T-cell exhaustion and antigen-presenting cell dysfunction), as well as resistance to therapy. Additionally, it has been found that nuclear localized PD-L2 (also referred to herein as "nuclear PD-L2" or "intranuclear PD-L2") co-localizes with at least one histone polypeptide (e.g., H2A, H2AX or H4) and that this co-localization is a surrogate marker for increased disease severity, decreased immunity and resistance to therapy (e.g., anti-infective therapy, cytotoxic therapy and/or immunotherapy). These findings have been reduced to practice in methods and kits for predicting the likelihood of response to therapy in a patient, as described hereafter.

Accordingly, in one aspect, the present disclosure provides methods for predicting the likelihood of response to a therapy (e.g., anti-infective therapy, cytotoxic therapy and/or immunotherapy) in a patient. These methods generally comprise, consist or consist essentially of analyzing cellular localization of PD-L2 in a PD-L2-expressing cell of the patient, to thereby predict the likelihood of response of the patient to the therapy. The PD-L2-expressing cell is suitably selected from an antigen-presenting cell (e.g., a DC), an immune effector cell (e.g., a B-cell or a T-cell) and a tumor cell. The therapy may be an anti-infective therapy, cytotoxic therapy or immunotherapy.

In some embodiments, the methods comprise detecting presence of PD-L2 in the nucleus of the cell or a level of PD-L2 in the nucleus of the cell, which is indicative of an aberrant or abnormal nuclear level of PD-L2 and which correlates with an increased likelihood of resistance to the therapy, to thereby determine that the patient has increased likelihood of resistance to the therapy. In some embodiments, the methods comprise detecting a higher level of PD-L2 relative to a control in the nucleus of the cell, to thereby determine that the patient has increased likelihood of resistance to the therapy. In some embodiments, the methods comprise comparing the level of PD-L2 between different cellular components (e.g., nucleus, cytoplasm, cell membrane), to thereby determine that the patient has increased likelihood of resistance to the therapy.

Suitably, the methods comprise detecting a higher level of PD-L2 in the nucleus of the cell relative to a control (e.g., relative to the nucleus of a corresponding normal or immunocompetent control cell, or relative to the level of PD-L2 outside the nucleus of the patient's cell such as the surface and/or cytoplasm of the cell), which indicates that the patient has increased likelihood of resistance to the therapy. In non-limiting examples of these embodiments, the higher level of PD-L2 in the nucleus of the cell represents a level that is at least about 120%, 130%, 140% 150%, 160%, 170%, 180%, 190%, 200%, 250%, 300%, 400%, 500%, 600%, 700%, 800%, 900%, or 1000% (and every integer in between) of the level of PD-L2 in the nucleus of the corresponding normal or immunocompetent control cell. In some of the same or other non-limiting examples of these embodiments, the higher level of PD-L2 in the nucleus of the cell represents a higher level of PD-L2 in the nucleus of the cell than outside the nucleus (e.g., surface and/or cytoplasm, collectively referred to herein as "extranuclear") of the cell. In representative examples of this type, the higher level is indicative of a ratio of nuclear PD-L2 to extranuclear PD-L2 of greater than about 0.55, 0.60, 0.65, 0.70, 0.75, 0.85, 0.90 or 0.95. In some of the same and other non-limiting examples, the methods comprise detecting a higher level of nuclear PD-L2 in more than 30%, 35%, 40%, 45%, 50%, 55%, 60%, 65%, 70%, 75%, 80%, 85%, 90%, or 95% of the patient's cells (e.g., antigen-presenting cells such as DCs, immune effector cells such as B-cells and T-cells, and/or tumor cells), which indicates that the patient has increased likelihood of resistance to the therapy.

In other embodiments, the methods comprise detecting absence of PD-L2 in the nucleus of the cell or a level of PD-L2 in the nucleus of the cell, which is indicative of a normal nuclear level of PD-L2 and which correlates with an increased likelihood of sensitivity to the therapy, to thereby determine that the patient has increased likelihood of sensitivity to the therapy. In some of the same and other embodiments, the methods comprise detecting a level of PD-L2 in the nucleus of the cell relative to a control (e.g., relative to the nucleus of a corresponding normal or immunocompetent cell, or relative to the levels of PD-L2 outside the nucleus of the patient's cell), which level is indicative of a normal nuclear level of PD-L2 and which indicates that the patient has increased likelihood of sensitivity to the therapy. In some of the same and other embodiments, the methods comprise detecting presence of PD-L2 outside the nucleus (e.g., surface and/or cytoplasm) of the cell to thereby determine that the patient has increased likelihood of sensitivity to the therapy. Suitably, the methods comprise detecting a level of PD-L2 outside the nucleus of the cell relative to a control (e.g., relative to outside the nucleus of a corresponding normal or immunocompetent cell, or relative to the levels of PD-L2 inside the nucleus of the patient's cell), which level is indicative of a normal extranuclear level of PD-L2 and which indicates that the patient has increased likelihood of sensitivity to the therapy. In non-limiting examples of these embodiments, the level of PD-L2 outside the nucleus of the cell represents a level that is about the same level (e.g., a level that is from about 85% to about 115%, and every integer in between) of PD-L2 outside the nucleus of the corresponding normal or immunocompetent control cell. In some of the same or other non-limiting examples of these embodiments, the level of PD-L2 outside the nucleus of the cell represents a higher level of PD-L2 outside the nucleus (e.g., surface and/or cytoplasm) of the cell than inside the nucleus of the cell. In representative examples of this type, the higher level is indicative of a ratio of extranuclear PD-L2 to nuclear PD-L2 of greater than about 0.55, 0.60, 0.65, 0.70, 0.75, 0.85, 0.90 or 0.95. In some of the same and other non-limiting examples, the methods comprise detecting a normal level of extranuclear PD-L2 in more than 30%, 35%, 40%, 45%, 50%, 55%, 60%, 65%, 70%, 75%, 80%, 85%, 90%, or 95% of the patient's cells (e.g., antigen-presenting cells such as DCs, immune effector cells such as B-cells and T-cells, and/or tumor cells), which indicates that the patient has increased likelihood of sensitivity to the therapy.

Suitably, in any of the above embodiments, the methods comprise detecting co-localization of PD-L2 with a nuclear binding partner of PD-L2 (e.g., a histone polypeptide representative examples of which include an H2A polypeptide, an H2AX polypeptide and an H4 polypeptide). In some examples of these embodiments, the methods comprise contacting a sample comprising a cell of the patient or lysate of the cell with a first antigen-binding molecule that binds specifically to PD-L2 and a second antigen-binding molecule that binds specifically to the nuclear binding partner, and detecting the presence in the sample of a complex that comprises the first antigen-binding molecule and the second antigen-binding molecule, to thereby determine that the patient has increased likelihood of resistance to the therapy. In some embodiment, the methods comprise detecting a higher level of the complex relative to a control (e.g., a corresponding normal or immunocompetent control cell), which indicates that the patient has increased likelihood of resistance to the therapy. In other embodiments, the methods comprise detecting a level of the complex in the nucleus relative to a control (e.g., a corresponding normal or immunocompetent control cell), which level is indicative of a normal level of the complex and which indicates that the patient has increased likelihood of sensitivity to the therapy.

Another aspect of the present disclosure provides methods for determining likelihood of resistance to a therapy (e.g., anti-infective therapy, cytotoxic therapy and/or immunotherapy) in a patient. These methods generally comprise, consist or consist essentially of detecting in a sample (e.g., a sample comprising a PD-L2-expressing cell such as an antigen-presenting cell, immune effector cell, or tumor cell, or lysate thereof) of the patient co-localization of PD-L2 with a nuclear binding partner of PD-L2 (e.g., a histone polypeptide representative examples of which include an H2A polypeptide, an H2AX polypeptide and an H4 polypeptide), or a level of the co-localization, which is indicative of an aberrant or abnormal level of the co-localization and which correlates with an increased likelihood of resistance to the therapy, to thereby determine that the patient has increased likelihood of resistance to the therapy. In some embodiments, the methods comprise detecting in the sample a higher level of the co-localization relative to a control (e.g., a reference sample comprising a corresponding normal or immunocompetent control PD-L2-expressing cell, or lysate thereof), to thereby determine that the patient has increased likelihood of resistance to the therapy. In other embodiments, the methods comprise detecting in the sample about the same level of the co-localization relative to a control (e.g., a reference sample comprising a corresponding PD-L2-expressing cell having an aberrant level of nuclear PD-L2, or lysate thereof), to thereby determine that the patient has increased likelihood of resistance to the therapy.

In a related aspect, the present disclosure provides methods for determining likelihood of resistance to a therapy (e.g., anti-infective therapy, cytotoxic therapy and/or immunotherapy) in a patient. These methods generally comprise, consist or consist essentially of detecting in a sample (e.g., a sample comprising a PD-L2-expressing cell such as an antigen-presenting cell, immune effector cell, or tumor cell, or lysate thereof) of the patient presence of a complex comprising PD-L2 and a nuclear binding partner of PD-L2 (e.g., a histone polypeptide representative examples of which include an H2A polypeptide, an H2AX polypeptide and an H4 polypeptide), or a level of the complex, which is indicative of an aberrant or abnormal level of the complex and which correlates with an increased likelihood of resistance to the therapy, to thereby determine that the patient has increased likelihood of resistance to the therapy. In some embodiments, the methods comprise detecting in the sample a higher level of the complex relative to a control (e.g., a reference sample comprising a corresponding normal or immunocompetent control PD-L2-expressing cell, or lysate thereof), to thereby determine that the patient has increased likelihood of resistance to the therapy. In other embodiments, the methods comprise detecting about the same level of the complex relative to a control (e.g., a reference sample comprising a corresponding PD-L2-expressing cell having an aberrant level of nuclear PD-L2, or lysate thereof), to thereby determine that the patient has increased likelihood of resistance to the therapy.

Yet another aspect of the present disclosure provides methods for determining likelihood of sensitivity to a therapy (e.g., anti-infective therapy, cytotoxic therapy and/or immunotherapy) in a patient. These methods generally comprise, consist or consist essentially of detecting in a sample (e.g., a sample comprising a PD-L2-expressing cell such as an antigen-presenting cell, immune effector cell, or tumor cell, or lysate thereof) of the patient absence of co-localization of PD-L2 with a nuclear binding partner of PD-L2 (e.g., a histone polypeptide representative examples of which include an H2A polypeptide, an H2AX polypeptide and an H4 polypeptide), or a level of the co-localization, which is indicative of a normal level of the co-localization and which correlates with an increased likelihood of sensitivity to the therapy, to thereby determine that the patient has increased likelihood of sensitivity to the therapy. In some embodiments, the methods comprise detecting about the same level of the co-localization relative to a control (e.g., a reference sample comprising a corresponding normal or immunocompetent control PD-L2-expressing cell, or lysate thereof) in a sample (e.g., a sample comprising an antigen-presenting cell, an immune effector cell, or a tumor cell, or lysate thereof) of the patient, to thereby determine that the patient has increased likelihood of sensitivity to the therapy. In other embodiments, the methods comprise detecting a lower level of the co-localization relative to a control (e.g., a reference sample comprising a corresponding control PD-L2-expressing cell having an aberrant level of nuclear PD-L2, or lysate thereof), to thereby determine that the patient has increased likelihood of sensitivity to the therapy.

In a related aspect, the present disclosure provides methods for determining likelihood of sensitivity to a therapy (e.g., anti-infective therapy, cytotoxic therapy and/or immunotherapy) in a patient. These methods generally comprise, consist or consist essentially of detecting in a sample (e.g., a sample comprising a PD-L2-expressing cell such as an antigen-presenting cell, immune effector cell, or tumor cell, or lysate thereof) of the patient absence of a complex comprising PD-L2 and a nuclear binding partner of PD-L2 (e.g., a histone polypeptide representative examples of which include an H2A polypeptide, an H2AX polypeptide and an H4 polypeptide), or a level of the complex, which is indicative of a normal level of the complex and which correlates with an increased likelihood of sensitivity to the therapy, to thereby determine that the patient has increased likelihood of sensitivity to the therapy. In some embodiments, the methods comprise detecting about the same level of the complex relative to a control (e.g., a reference sample comprising a corresponding normal or immunocompetent control PD-L2-expressing cell, or lysate thereof), to thereby determine that the patient has increased likelihood of sensitivity to the therapy. In other embodiments, the methods comprise detecting a lower level of the complex relative to a control (e.g., a reference sample comprising a corresponding control PD-L2-expressing cell having an aberrant level of nuclear PD-L2, or lysate thereof), to thereby determine that the patient has increased likelihood of sensitivity to the therapy.

In another aspect, the present disclosure provides methods for analyzing cellular localization of PD-L2 (e.g., in an antigen-presenting cell, an immune effector cell, or tumor cell). These methods generally comprise, consist or consist essentially of detecting the presence, absence or level of co-localization of PD-L2 with a nuclear binding partner of PD-L2 (e.g., a histone polypeptide representative examples of which include an H2A polypeptide, an H2AX polypeptide and an H4 polypeptide) in a cell, to thereby determine localization of PD-L2 in the cell. In some embodiments, presence of the co-localization is indicative of nuclear localization of PD-L2. In other embodiments, absence of the co-localization is indicative of extranuclear localization of PD-L2. In still other embodiments, the methods comprise detecting a normal level of the co-localization relative to a control (e.g., the level of co-localization in a corresponding normal or immunocompetent cell, or lysate thereof) which indicates that that there is a higher extranuclear localization of PD-L2 than nuclear localization of PD-L2. In still other embodiments, the methods comprise detecting a higher level of the co-localization relative to a control (e.g., the level of co-localization in a corresponding normal or immunocompetent cell, or lysate thereof) which indicates that that there is a higher nuclear localization of PD-L2 than extranuclear localization of PD-L2. In representative examples of these embodiments, the co-localization is represented by a complex comprising PD-L2 and the nuclear binding partner of PD-L2.

Still another aspect of the present disclosure provides methods for stratifying a patient as a likely responder or non-responder to a therapy (e.g., anti-infective therapy, cytotoxic therapy and/or immunotherapy). These methods generally comprise, consist or consist essentially of: analyzing cellular localization of PD-L2 as broadly described above and elsewhere herein in a sample of the patient, to determine whether the patient has increased likelihood of sensitivity or resistance to the therapy, to thereby stratify the patient as a likely responder or non-responder to the therapy.

A further aspect of the present disclosure provides methods for managing treatment of a patient with a therapy (e.g., anti-infective therapy, cytotoxic therapy and/or immunotherapy). These methods generally comprise, consist or consist essentially of: selecting a patient for treating with the therapy on the basis that the patient is a likely responder to the therapy, or selecting a patient for not treating with the therapy on the basis that the patient is a likely non-responder to the therapy and treating or not treating the patient with the therapy based on the selection, wherein the selection is based on the stratification method broadly described above and elsewhere herein.

In another aspect of the present disclosure, methods are provided for predicting treatment outcome of a patient with a therapy (e.g., anti-infective therapy, cytotoxic therapy and/or immunotherapy). These methods generally comprise, consist or consist essentially of: analyzing cellular localization of PD-L2 as broadly described above and elsewhere herein in a sample of the patient, to determine whether the patient has increased likelihood of sensitivity or resistance to the therapy, to thereby predict the treatment outcome for the patient. In some embodiments, the methods comprise detecting presence or a level of nuclear-localized PD-L2 relative to a control, which correlates with an increased likelihood of resistance to the therapy, as broadly described above and elsewhere herein, and predicting a negative treatment outcome. Suitably, the negative treatment outcome is greater disease severity or progressive disease. In other embodiments, the methods comprise detecting absence or a level of nuclear-localized PD-L2 relative to a control, which correlates with an increased likelihood of sensitivity to the therapy, as broadly described above and elsewhere herein, and predicting a positive treatment outcome. The positive treatment outcome may be selected from a partial or complete response to the therapy and stable disease. In any of these embodiments, the methods suitably further comprise predicting a clinical outcome for the patient based on the predicted treatment outcome. In non-limiting examples of this type, the patient is a cancer patient and the clinical outcome is selected from tumor response (TR), overall survival (OS), progression free survival (PFS), disease free survival, time to tumor recurrence (TTR), time to tumor progression (TTP), relative risk (RR), toxicity or side effect.

A further aspect of the present disclosure provides methods of monitoring a disease in a patient following treatment with a therapy. These methods generally comprise, consist or consist essentially of: obtaining a sample from the patient following treatment of the patient with the therapy (e.g., anti-infective therapy, cytotoxic therapy and/or immunotherapy), wherein the sample comprises a PD-L2-expressing cell (e.g., in an antigen-presenting cell, an immune effector cell, or tumor cell); analyzing cellular localization of PD-L2 as broadly described above and elsewhere herein in the sample, wherein a lower level of nuclear-localized PD-L2 relative to a control sample of the patient taken prior to the treatment is indicative of an increased clinical benefit of the therapy (e.g., lesser disease severity, delaying progression of the disease, reduced rate of disease progression, or absence or amelioration of the disease) to the patient and wherein a similar or higher level of nuclear-localized PD-L2 relative to the control sample is indicative of no or negligible clinical benefit of the therapy to the subject.

Yet a further aspect of the present disclosure provides methods for determining status of a disease in a patient. These methods generally comprise, consist or consist essentially of: analyzing cellular localization of PD-L2 as broadly described above and elsewhere herein in a sample of the patient, to thereby determine the status of the disease in the patient, wherein presence or a level of nuclear-localized PD-L2, which correlates with an increased likelihood of resistance to a therapy, as broadly described above and elsewhere herein, indicates greater severity or progression of the disease in the patient and wherein absence or a level of nuclear-localized PD-L2, which correlates with an increased likelihood of sensitivity to a therapy, as broadly described above and elsewhere herein, indicates absence of the disease or lesser severity or progression of the disease in the patient.

Still another aspect of the present disclosure provides methods for determining immune status of a patient. These methods generally comprise, consist or consist essentially of: analyzing cellular localization of PD-L2 as broadly described above and elsewhere herein in a sample of the patient, to thereby determine the immune status of the patient, wherein presence or a level of nuclear-localized PD-L2, which correlates with an increased likelihood of resistance to a therapy, as broadly described above and elsewhere herein, indicates that the patient is immunocompromised or has reduced immunity (e.g., immune dysfunction including T-cell dysfunction such as T-cell exhaustion and antigen-presenting cell dysfunction) and wherein absence or a level of nuclear-localized PD-L2 relative, which correlates with an increased likelihood of sensitivity to a therapy, as broadly described above and elsewhere herein indicates that the patient is immunocompetent.

Yet another aspect of the present disclosure provides kits for detecting location of PD-L2 in a cellular location (e.g., surface, cytoplasm or nucleus) of a cell, for predicting the likelihood of response of a cell to a therapy (e.g., anti-infective therapy, cytotoxic therapy and/or immunotherapy), for determining likelihood of resistance of a patient to a therapy (e.g., anti-infective therapy, cytotoxic therapy and/or immunotherapy), for determining likelihood of sensitivity of a patient to a therapy (e.g., anti-infective therapy, cytotoxic therapy and/or immunotherapy), for stratifying a patient as a likely responder or non-responder to a therapy (e.g., anti-infective therapy, cytotoxic therapy and/or immunotherapy), for managing treatment of a patient with a therapy (e.g., anti-infective therapy, cytotoxic therapy and/or immunotherapy), for monitoring a disease in a patient following treatment with a therapy, for determining the status of a disease in a patient and/or for determining the immune status of a patient. These kits generally comprise, consist or consist essentially of: a first antigen-binding molecule that binds specifically to PD-L2. In some embodiments, the kits comprise a second antigen-binding molecule that binds specifically to a nuclear binding partner of PD-L2 (e.g., a histone polypeptide representative examples of which include an H2A polypeptide, an H2AX polypeptide and an H4 polypeptide). In some embodiments, the kits further comprise a third antigen-binding molecule, which suitably comprises a detectable label, that binds to the first and second antigen-binding molecules. Suitably, the kits of further comprise instructional material for performing any one or more of the methods broadly described above and elsewhere herein.

Still another aspect of the present disclosure provides a complex comprising PD-L2 and a nuclear binding partner of PD-L2 (e.g., an H2A polypeptide, an H2AX polypeptide or an H4 polypeptide), a first antigen-binding molecule that is bound specifically to PD-L2 of the complex and a second antigen-binding molecule bound to the nuclear binding partner of the complex. In some embodiments, the complex is located in a cell or lysate thereof. Suitably, the complex further comprises a third antigen-binding molecule, which is suitably detectably labeled, that binds to each of the first and second antigen-binding molecules of the complex.

In a further aspect, the present disclosure provides a cell or lysate thereof, comprising a complex broadly described above and elsewhere herein.

In certain embodiments of any of the above aspects, the therapy comprises an immunotherapy (e.g., an immune checkpoint inhibitor such as an antagonist antigen-binding molecule that binds specifically to an immune checkpoint molecule). In illustrative examples of this type, the immunotherapy comprises an antagonist antigen-binding molecule that binds specifically to PD-1. In certain embodiments of any of the above aspects, the therapy comprises a cytotoxic therapy (e.g., a chemotherapeutic agent). In certain embodiments of any of the above aspects, the therapy comprises an anti-infective therapy (e.g., an anti-protozoal agent such as an anti-malarial agent).

Figure 1:
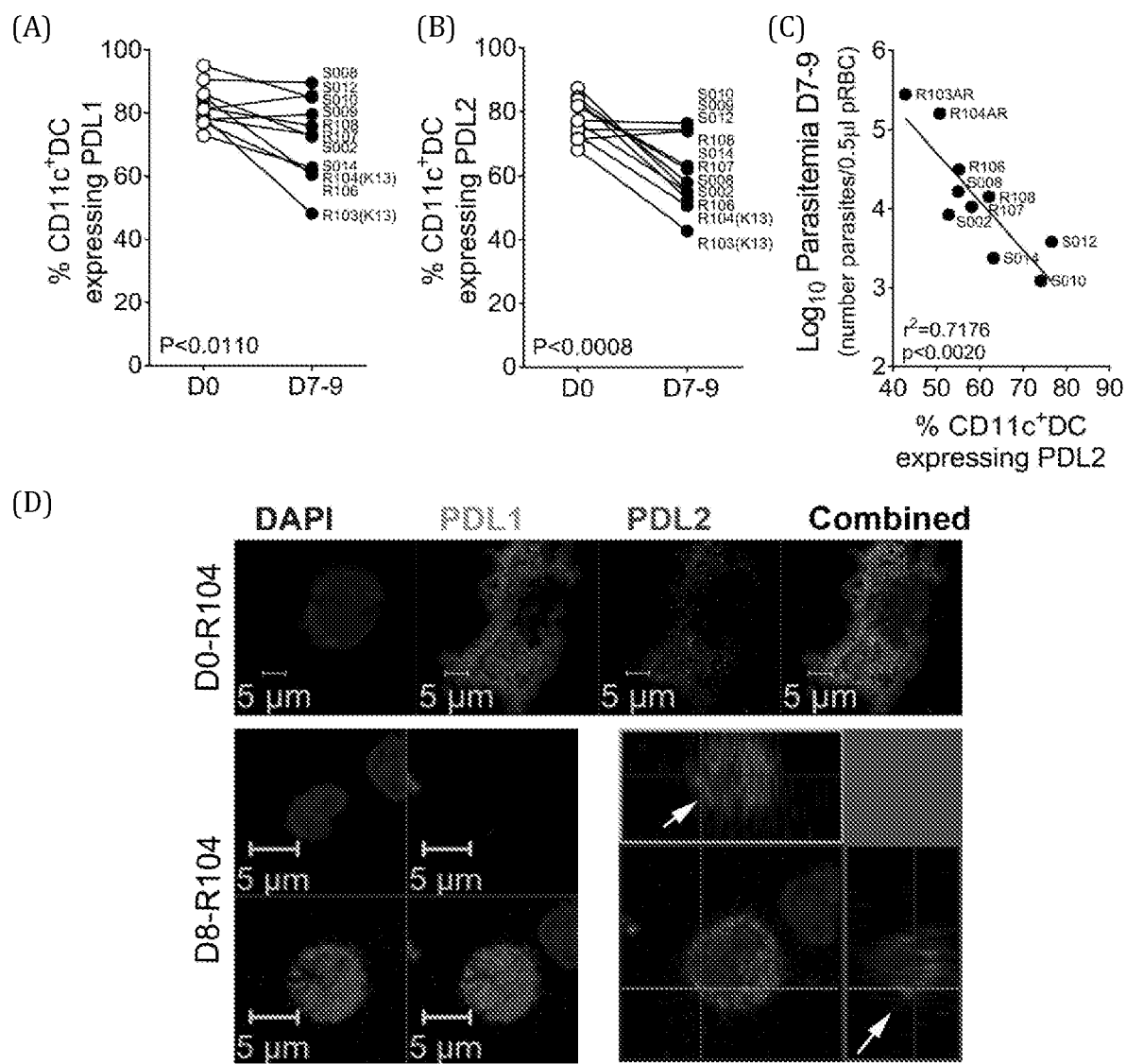
FIG. 1 is a graphical and photographic representation showing that nuclear PD-L2 in DCs from malaria-infected volunteers is associated with poor parasite control. Eleven healthy human volunteers were inoculated with *P. falciparum* and blood examined for percentage of CD11c$^+$ DC expressing (A) PD-L1 and (B) PD-L2, before and 7-9 days after infection, just before drug treatment. (C) Plot showing number of parasites/0.5 µL blood versus % CD11c$^+$ DCs expressing PD-L2. R1O3 to R108 and S002-S008 represents each volunteer in 2 different studies with K13 indicating a different parasite strain. The P value is testing the null hypothesis that the overall slope is zero. (D) Representative microscopy from volunteer R104 showing DCs expressing PD-L1 and PD-L2 before infection and 9 days after infection which revealed nuclear PD-L2. The orthogonal view with blue, red and green lines highlights a point in 3D z-stack where red PD-L2 co-localizes with blue of DAPI in nuclei. Arrow indicates the site of co-localization. Significance between matched D0 and D7-9 human samples was analyzed by Wilcoxon matched-pairs signed rank test.

Some figures and text contain color representations or entities. Color illustrations are available from the Applicant upon request or from an appropriate Patent Office. A fee may be imposed if obtained from a Patent Office.

DETAILED DESCRIPTION

1. Definitions

Unless defined otherwise, all technical and scientific terms used herein have the same meaning as commonly understood by those of ordinary skill in the art to which the disclosure relates. Although any methods and materials similar or equivalent to those described herein can be used in the practice or testing of the disclosed products, methods or uses, preferred products, methods or uses are described. For the purposes of the present disclosure, the following terms are defined below.

The articles "a" and "an" are used herein to refer to one or to more than one (i.e. to at least one) of the grammatical object of the article. By way of example, "an element" means one element or more than one element.

The term "about" as used herein refers to the usual error range for the respective value readily known to the skilled person in this technical field. Reference to "about" a value or parameter herein includes (and describes) embodiments that are directed to that value or parameter per se.

The terms "administration concurrently" or "administering concurrently" or "co-administering" and the like refer to the administration of a single composition containing two or more actives, or the administration of each active as separate compositions and/or delivered by separate routes either contemporaneously or simultaneously or sequentially within a short enough period of time that the effective result is equivalent to that obtained when all such actives are administered as a single composition. By "simultaneously" is meant that the active agents are administered at substantially the same time, and desirably together in the same formulation. By "contemporaneously" it is meant that the active agents are administered closely in time, e.g., one agent is administered within from about one minute to within about one day before or after another. Any contemporaneous time is useful. However, it will often be the case that when not administered simultaneously, the agents will be administered within about one minute to within about eight hours and suitably within less than about one to about four hours. When administered contemporaneously, the agents are suitably administered at the same site on the subject. The term "same site" includes the exact location, but can be within about 0.5 to about 15 centimeters, preferably from within about 0.5 to about 5 centimeters. The term "separately" as used herein means that the agents are administered at an interval, for example at an interval of about a day to several weeks or months. The active agents may be administered in either order. The term "sequentially" as used herein means that the agents are administered in sequence, for example at an interval or intervals of minutes, hours, days or weeks. If appropriate the active agents may be administered in a regular repeating cycle.

The term "agent" includes a compound that induces a desired pharmacological and/or physiological effect. The term also encompass pharmaceutically acceptable and pharmacologically active ingredients of those compounds specifically mentioned herein including but not limited to salts, esters, amides, prodrugs, active metabolites, analogs and the like. When the above term is used, then it is to be understood that this includes the active agent per se as well as pharmaceutically acceptable, pharmacologically active salts, esters, amides, prodrugs, metabolites, analogs, etc. The term "agent" is not to be construed narrowly but extends to small molecules, proteinaceous molecules such as peptides, polypeptides and proteins as well as compositions comprising them and genetic molecules such as RNA, DNA and mimetics and chemical analogs thereof as well as cellular agents. The term "agent" includes a cell that is capable of producing and secreting a polypeptide referred to herein as well as a polynucleotide comprising a nucleotide sequence that encodes that polypeptide. Thus, the term "agent" extends to nucleic acid constructs including vectors such as viral or non-viral vectors, expression vectors and plasmids for expression in and secretion in a range of cells.

"Amplification," as used herein generally refers to the process of producing multiple copies of a desired sequence. "Multiple copies" mean at least two copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

The "amount" or "level" of a biomarker is a detectable level in a sample. These can be measured by methods known to one skilled in the art and also disclosed herein. The expression level or amount of biomarker assessed can be used to determine the response to treatment.

As used herein, "and/or" refers to and encompasses any and all possible combinations of one or more of the associated listed items, as well as the lack of combinations when interpreted in the alternative (or).

The term "antagonist" or "inhibitor" refers to a substance that prevents, blocks, inhibits, neutralizes, or reduces a biological activity or effect of another molecule, such as an enzyme or receptor.

The term "antagonist antibody" refers to an antibody that binds to a target and prevents or reduces the biological effect of that target. In some embodiments, the term can denote an antibody that prevents the target, e.g., PD-1, to which it is bound from performing a biological function.

As used herein, an "anti-PD-1 antagonist antibody" refers to an antibody that is able to inhibit PD-1 biological activity and/or downstream events(s) mediated by PD-1. Anti-PD-1 antagonist antibodies encompass antibodies that block, antagonize, suppress or reduce (to any degree including significantly) PD-1 biological activity, including inhibitory signal transduction through PD-1 and downstream events mediated by PD-1, such as PD-L1 binding and downstream signaling, PD-L2 binding and downstream signaling, inhibition of T-cell proliferation, inhibition of T-cell activation, inhibition of IFN secretion, inhibition of IL-2 secretion, inhibition of TNF secretion, induction of IL-10, and inhibition of anti-tumor immune responses. For purposes of the present disclosure, it will be explicitly understood that the term "anti-PD-1 antagonist antibody" (interchangeably termed "antagonist PD-1 antibody", "antagonist anti-PD-1 antibody" or "PD-1 antagonist antibody") encompasses all the previously identified terms, titles, and functional states and characteristics whereby PD-1 itself, a PD-1 biological activity, or the consequences of the biological activity, are substantially nullified, decreased, or neutralized in any meaningful degree. In some embodiments, an anti-PD-1 antagonist antibody binds PD-1 and upregulates an anti-tumor or anti-infective immune response. Examples of anti-PD-1 antagonist antibodies are provided herein.

The term "antibody" herein is used in the broadest sense and specifically covers monoclonal antibodies (including full length monoclonal antibodies), polyclonal antibodies, chimeric antibodies, humanized antibodies, human antibodies, multispecific antibodies (e.g., bispecific antibodies), and antibody fragments so long as they exhibit the desired biological activity.

As used herein, the term "antigen" and its grammatically equivalents expressions (e.g., "antigenic") refer to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

The term "antigen presenting cells" (APCs) refers to a class of cells capable of presenting one or more antigens in the form of peptide-MHC complex recognizable by specific effector cells of the immune system (also referred to herein as "immune effector cells"), and thereby modulating (e.g., stimulating/enhancing or reducing/tolerizing/anergizing) an immune response to the antigen or antigens being presented. In specific embodiments of the present disclosure, the APCs are capable of activating immune effector cells such as T lymphocytes, including $CD8^+$ and/or $CD4^+$ lymphocytes. Cells that have in vivo the potential to act as APC include, for example, not only professional APCs such as dendritic cells, macrophages, Langerhans cell, monocytes and B cells but also non-professional APCs illustrative examples of which include activated epithelial cells, fibroblasts, glial cells, pancreatic beta cells and vascular endothelial cells. Many types of cells are capable of presenting antigens on their cell surface for immune effector cell, including T-cell, recognition.

The term "anti-infective agent" as used herein refers to an agent that is capable of inhibiting the spread of an infectious agent such as an infectious microorganism, e.g., a bacteria, a virus, a nematode, a parasite, etc. Exemplary anti-infective agents may include anti-microbial agents, antibiotic agents, anti-viral, anti-fungal agents, anti-tuberculosis agents, anti-helminthic agents, anti-protozoal agents and anti-nematode agents. Illustrative antibiotic agents include quinolones (e.g., amifloxacin, cinoxacin, ciprofloxacin, enoxacin, fleroxacin, flumequine, lomefloxacin, nalidixic acid, norfloxacin, ofloxacin, levofloxacin, lomefloxacin, oxolinic acid, pefloxacin, rosoxacin, temafloxacin, tosufloxacin, sparfloxacin, clinafloxacin, gatifloxacin, moxifloxacin; gemifloxacin; and garenoxacin), tetracyclines, glycylcyclines and oxazolidinones (e.g., chlortetracycline, demeclocycline, doxycycline, lymecycline, methacycline, minocycline, oxytetracycline, tetracycline, tigecycline; linezolide, eperozolid), glycopeptides, aminoglycosides (e.g., amikacin, arbekacin, butirosin, dibekacin, fortimicins, gentamicin, kanamycin, meomycin, netilmicin, ribostamycin, sisomicin, spectinomycin, streptomycin, tobramycin), β-lactams (e.g., imipenem, meropenem, biapenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime, cefsulodin, ceftazidime, cefteram, ceftezole, ceftibuten, ceftizoxime, ceftriaxone, cefuroxime, cefuzonam, cephaacetrile, cephalexin, cephaloglycin, cephaloridine, cephalothin, cephapirin, cephradine, cefinetazole, cefoxitin, cefotetan, azthreonam, carumonam, flomoxef, moxalactam, amidinocillin, amoxicillin, ampicillin, azlocillin, carbenicillin, benzylpenicillin, carfecillin, cloxacillin, dicloxacillin, methicillin, mezlocillin, nafcillin, oxacillin, penicillin G, piperacillin, sulbenicillin, temocillin, ticarcillin, cefditoren, SC004, KY-020, cefdinir, ceftibuten, FK-312, S-1090, CP-0467, BK-218, FK-037, DQ-2556, FK-518, cefozopran, ME1228, KP-736, CP-6232, Ro 09-1227, OPC-20000, LY206763), rifamycins, macrolides (e.g., azithromycin, clarithromycin, erythromycin, oleandomycin, rokitamycin, rosaramicin, roxithromycin, troleandomycin), ketolides (e.g., telithromycin, cethromycin), coumermycins, lincosamides (e.g., clindamycin, lincomycin) and chloramphenicol.

Illustrative anti-viral agents include abacavir sulfate, acyclovir sodium, amantadine hydrochloride, amprenavir, cidofovir, delavirdine mesylate, didanosine, efavirenz, famciclovir, fomivirsen sodium, foscarnet sodium, ganciclovir, indinavir sulfate, lamivudine, lamivudine/zidovudine, nelfinavir mesylate, nevirapine, oseltamivir phosphate, ribavirin, rimantadine hydrochloride, ritonavir, saquinavir, saquinavir mesylate, stavudine, valacyclovir hydrochloride, zalcitabine, zanamivir, and zidovudine.

Non-limiting examples of amebicides or anti-protozoal agents include atovaquone, chloroquine hydrochloride, chloroquine phosphate, metronidazole, metronidazole hydrochloride, and pentamidine isethionate. Representative anti-helminthic agents are suitably selected from mebendazole, pyrantel pamoate, albendazole, ivermectin and thiabendazole. Illustrative antifungals can be selected from amphotericin B, amphotericin B cholesteryl sulfate complex, amphotericin B lipid complex, amphotericin B liposomal, fluconazole, flucytosine, griseofulvin microsize, griseofulvin ultramicrosize, itraconazole, ketoconazole, nystatin, and terbinafine hydrochloride. Non-limiting examples of antimalarials include chloroquine hydrochloride, chloroquine phosphate, doxycycline, hydroxychloroquine sulfate, mefloquine hydrochloride, primaquine phosphate, pyrimethamine, and pyrimethamine with sulfadoxine. Anti-tuberculosis agents include but are not restricted to clofazimine, cycloserine, dapsone, ethambutol hydrochloride, isoniazid, pyrazinamide, rifabutin, rifampin, rifapentine, and streptomycin sulfate.

As use herein, the term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of $\leq 1$ μM, $\leq 100$ nM, $\leq 10$ nM, $\leq 1$ nM, or $\leq 0.1$ nM. In certain embodiments, an antibody specifically binds to an epitope on a protein that is conserved among the protein from different species. In another embodiment, specific binding can include, but does not require exclusive binding.

The term "biomarker" as used herein refers to an indicator, e.g., predictive, diagnostic, and/or prognostic, which can be detected in a sample.

The terms "cancer" and "cancerous" refer to or describe the physiological condition in subjects that is typically characterized by unregulated cell growth. Examples of cancer include but are not limited to, carcinoma, lymphoma, blastoma, sarcoma, and leukemia or lymphoid malignancies. More particular examples of such cancers include, but not limited to, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo malignant melanoma, acral lentiginous melanomas, nodular melanomas, multiple myeloma and B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenström's Macroglobulinemia); chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phacomatoses, edema (such as that associated with brain tumors), Meigs' syndrome, brain, as well as head and neck cancer, and associated metastases. In certain embodiments, cancers that are amenable to treatment by the antibodies of the disclosure include breast cancer, colorectal cancer, rectal cancer, non-small cell lung cancer, glioblastoma, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, ovarian cancer, mesothelioma, and multiple myeloma. In some embodiments, the cancer is selected from: small cell lung cancer, glioblastoma, neuroblastomas, melanoma, breast carcinoma, gastric cancer, colorectal cancer (CRC), and hepatocellular carcinoma. Yet, in some embodiments, the cancer is selected from: non-small cell lung cancer, colorectal cancer, glioblastoma and breast carcinoma, including metastatic forms of those cancers. In specific embodiments, the cancer is melanoma or colorectal cancer, suitably metastatic melanoma or metastatic colorectal cancer.

"Chemotherapeutic agent" includes compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-α, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG₁λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-α for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quin-azolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoli-ne, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol)-; (R)-6-(4-hydroxyphenyl)-4-[(1-phenylethyl)amino]-7H-pyrrolo[2,3-d]pyrimi-dine); CL-387785 (N-[4-[(3-bromophenyl)amino]-6-quinazolinyl]-2-butyna-mide); EKB-569 (N-[4-[(3-chloro-4-fluorophenyl)amino]-3-cyano-7-ethoxy-6-quinolinyl]-4-(-dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from GlaxoSmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035, 4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor α (TNF-α) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T-cell costimulation blockers such as abatacept (Orencia), Interleukin 6 (IL-6) blockers such as tocilizumab (ACTEMERA®); Interleukin 13 (IL-13) blockers such as lebrikizumab; Interferon α (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin α (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH$_3$, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhea, metastatic bone pain, headache and migraine, postoperative pain, mild-to-moderate pain due to inflammation and tissue injury, pyrexia, ileus, and renal colic.

The term "chemotherapy" refers to medical treatment of a human or animal with one or more chemotherapeutic agents.

As used herein, the term "co-localization" or "co-localized" refers two or more molecules having identical or overlapping localization in the cell. Co-localization of molecules and proteins can be detected using any suitable method known in the art, including for example, fluorescent microscopy in fixed or living cells. For example, PD-L2 and a PD-2 nuclear binding partner(e.g., a histone polypeptide such as but not limited to an H2A polypeptide, an H2AX polypeptide or an H4 polypeptide) can be co-localized in cells using fluorescently-labeled anti-PD-L2 and anti-nuclear binding partner primary antibodies and optionally one or more secondary antibodies. Methods of co-localization of cellular molecules are well known.

As used herein, a "companion diagnostic" refers to a diagnostic method and or reagent that is used to identify subjects susceptible to treatment with a particular treatment or to monitor treatment and/or to identify an effective dosage for a subject or sub-group or other group of subjects. For purposes herein, a companion diagnostic refers to reagents, such as a reagent for detecting or measuring PD-L2 cellular localization (e.g., as described herein) in a sample. The companion diagnostic refers to the reagents and also to the test(s) that is/are performed with the reagent.

As used herein, the term "complex" refers to an assemblage or aggregate of molecules (e.g., peptides, polypeptides, etc.) in direct and/or indirect contact with one another. In specific embodiments, "contact", or more particularly, "direct contact" means two or more molecules are close enough so that attractive noncovalent interactions, such as Van der Waal forces, hydrogen bonding, ionic and hydrophobic interactions, and the like, dominate the interaction of the molecules. In such embodiments, a complex of molecules (e.g., a peptide and polypeptide) is formed under conditions such that the complex is thermodynamically favored (e.g., compared to a non-aggregated, or non-complexed, state of its component molecules). The term "polypeptide complex" or "protein complex," as used herein, refers to a trimer, tetramer, pentamer, hexamer, heptamer, octamer, nonamer, decamer, undecamer, dodecamer, or higher order oligomer. In specific embodiments, the polypeptide complexes are formed by self-assembly of PD-L2 and a nuclear binding partner of PD-L2 (e.g., an H2A polypeptide, an H2AX polypeptide or an H4 polypeptide).

Throughout this specification, unless the context requires otherwise, the words "comprise," "comprises" and "comprising" will be understood to imply the inclusion of a stated step or element or group of steps or elements but not the exclusion of any other step or element or group of steps or elements. Thus, use of the term "comprising" and the like indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "correlate" or "correlating" refer to determining a relationship between one type of data with another or with a state (e.g., mesenchymal state, immune status inclusive of T-cell activation, immunocompetence, immune dysfunction including T-cell dysfunction such as T-cell exhaustion and antigen-presenting cell dysfunction, response to therapy, disease severity or progression, etc.). In some embodiments, "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of polypeptide analysis or protocol, one may use the results of the polypeptide expression or cellular localization analysis or protocol to determine whether a specific therapeutic regimen should be performed.

The term "cytotoxic agent" as used herein refers to any agent that is detrimental to cells (e.g., causes cell death, inhibits proliferation, or otherwise hinders a cellular function). Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof. Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A, inhibitors of fatty acid biosynthesis, cell cycle signaling inhibitors, HDAC inhibitors, proteasome inhibitors, and inhibitors of cancer metabolism. In some embodiments, the cytotoxic agent is a taxane. In representative examples of this type, the taxane is paclitaxel or docetaxel. In some embodiments, the cytotoxic agent is a platinum agent. In some embodiments, the cytotoxic agent is an antagonist of EGFR. In representative examples of this type, the antagonist of EGFR is N-(3-ethynylphenyl)-6,7-bis(2-methoxyethoxy)quinazolin-4-amine (e.g., erlotinib). In some embodiments, the cytotoxic agent is a RAF inhibitor. In non-limiting examples of this type, the RAF inhibitor is a BRAF and/or CRAF inhibitor. In other non-limiting examples, the RAF inhibitor is vemurafenib. In one embodiment the cytotoxic agent is a PI3K inhibitor.

As used herein, the term "cytotoxic therapy" refers to therapies that induce cellular damage including but not limited to radiation, chemotherapy, photodynamic therapy, radiofrequency ablation, anti-angiogenic therapy, and combinations thereof. A cytotoxic therapeutic may induce DNA damage when applied to a cell.

As used herein, "delaying progression of a disease" or "decreasing the rate of progression of a disease" means to defer, hinder, slow, retard, stabilize, and/or postpone development of the disease (e.g., a cancer or pathogenic infection). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

The term "detection" includes any means of detecting, including direct and indirect detection.

The term "diagnosis" is used herein to refer to the identification or classification of a molecular or pathological state, disease or condition (e.g., cancer, pathogenic infection, immune dysfunctional disorder including a T-cell dysfunctional disorder and an antigen-presenting cell dysfunctional disorder, etc.). For example, "diagnosis" may refer to identification of a particular type of cancer, pathogenic infection, and immune dysfunctional disorder. "Diagnosis" may also refer to the classification of a particular subtype of cancer, pathogenic infection or immune dysfunctional disorder, e.g., by histopathological criteria, or by molecular features (e.g., a subtype characterized by localization of PD-L2 in one or more cellular components (e.g., nucleus, cytoplasm, plasma membrane, etc.), or by the presence, absence or level of a complex comprising PD-L2 and a PD-L2 nuclear binding partner). The term "aiding diagnosis" is used herein to refer to methods that assist in making a clinical determination regarding the presence, or nature, of a particular type of symptom or condition of a disease or disorder (e.g., cancer, pathogenic infection, immune dysfunctional disorder, etc.). For example, a method of aiding diagnosis of a disease or condition (e.g., cancer, pathogenic infection, immune dysfunctional disorder, etc.) can comprise determining cellular localization of PD-L2 (e.g., nucleus, cytoplasm, plasma membrane, etc.), or detecting the presence, absence or level of a complex comprising PD-L2 and a PD-L2 nuclear binding partner in a biological sample from an individual.

A "disorder" is any condition that would benefit from treatment including, but not limited to, chronic and acute disorders or diseases including those pathological conditions which predispose a subject to the disorder in question.

The term "dysfunction" in the context of immune dysfunction, refers to a state of reduced immune responsiveness to antigenic stimulation. The term includes reduced or compromised immune effector cell function and/or antigen-presenting cell function and encompasses the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into down-stream immune effector cell functions, including T-cell effector functions, such as proliferation, cytokine production (e.g., IL-2, IFN-γ, TNF-α, etc.) and/or target cell killing.

An "effective response" of a patient or a patient's "responsiveness" to treatment with a medicament and similar wording refers to the clinical or therapeutic benefit imparted to a patient at risk for, or suffering from, a disease or disorder, such as cancer, pathogenic infection, or immune dysfunctional disorder. In one embodiment, such benefit includes any one or more of: extending survival (including overall survival and progression free survival); resulting in an objective response (including a complete response or a partial response); or improving signs or symptoms of cancer. A patient who "does not have an effective response" to treatment refers to a patient who does not have any one of extending survival (including overall survival and progression free survival); resulting in an objective response (including a complete response or a partial response); or improving signs or symptoms of cancer.

The term "engineered autologous cell therapy", also known as adoptive cell transfer, is a process by which a patient's own T-cells are collected and subsequently genetically altered to recognize and target one or more antigens, e.g., one or more antigens expressed by a virus or on the cell surface of one or more specific tumor cells or malignancies. T-cells can be engineered to express, for example, chimeric antigen receptors (CAR) or T-cell receptor (TCR). CAR$^+$ T-cells are engineered to express an extracellular single chain variable fragment (scFv) with specificity for a particular antigen (e.g., a tumor antigen) linked to an intracellular signaling part comprising a costimulatory domain and an activating domain. The costimulatory domain can be derived from, e.g., CD28, and the activating domain can be derived from, e.g., CD3–zeta. Illustrative CAR$^+$ T-cell therapies and constructs as well as methods of their production are described in U.S. Patent Publication Nos. 2013/0287748, 2014/0227237, 2014/0099309, 2014/0050708 and 2015/0344844.

"Enhancing T-cell function" means to induce, cause or stimulate a T-cell to have a sustained or amplified biological function, or renew or reactivate exhausted or inactive T-cells. Examples of enhancing T-cell function include any one or more of: increased secretion of IFN-γ, increased secretion of TNF-α, increased secretion of IL-2 from CD8$^+$ T-cells, increased proliferation, increased antigen responsiveness (e.g., viral, pathogen, or tumor clearance) relative to such levels before the intervention. In some embodiments, the level of enhancement is as least 50%, alternatively 60%, 70%, 80%, 90%, 100%, 120%, 150%, 200%. The manner of measuring this enhancement is known to one of ordinary skill in the art.

The term "exhaustion" and its grammatical equivalents refer to T-cell exhaustion as a state of T-cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T-cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

As used herein, the term "higher" with reference to a biomarker or biomarker complex measurement refers to a statistically significant and measurable difference in the level of a biomarker or biomarker complex measurement compared to the level of another biomarker or biomarker complex or to a control level where the biomarker or biomarker complex measurement is greater than the level of the other biomarker or biomarker complex or the control level. The difference is preferably at least about 10%, or at least about 20%, or of at least about 30%, or of at least about 40%, or at least about 50%.

The term "immune effector cells" in the context of the present disclosure relates to cells which exert effector functions during an immune reaction. For example, such cells secrete cytokines and/or chemokines, kill microbes, secrete antibodies, recognize infected or cancerous cells, and optionally eliminate such cells. For example, immune effector cells comprise T-cells (cytotoxic T-cells, helper T-cells, tumor infiltrating T-cells), B-cells, natural killer (NK) cells, lymphokine-activated killer (LAK) cells, neutrophils, macrophages, and dendritic cells.

The term "immune effector function" in the context of the present disclosure includes any function mediated by components of the immune system that result, for example, in the killing of virally infected cells or tumor cells, or in the inhibition of tumor growth and/or inhibition of tumor development, including inhibition of tumor dissemination and metastasis. In some embodiments, the immune effector function in the context of the present disclosure is a T-cell mediated effector function. Such functions comprise in the case of a helper T-cell (CD4$^+$ T-cell) the recognition of an antigen or an antigen peptide derived from an antigen in the context of MHC class II molecules by T-cell receptors, the release of cytokines and/or the activation of CD8$^+$ lymphocytes (CTLs) and/or B-cells, and in the case of CTL the recognition of an antigen or an antigen peptide derived from an antigen in the context of MHC class I molecules by T-cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

A used herein, the term "immune response" refers to a response by the immune system of a subject. For example, immune responses include, but are not limited to, a detectable alteration (e.g., increase) in Toll receptor activation, lymphokine (e.g., cytokine (e.g., Th1 or Th2 type cytokines) or chemokine) expression and/or secretion, macrophage activation, dendritic cell activation, T-cell activation (e.g., CD4$^+$ or CD8$^+$ T-cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T-cells, B cells (e.g., of any stage of development (e.g., plasma cells), and increased processing and presentation of antigen by antigen presenting cells. An immune response may be to immunogens that the subject's immune system recognizes as foreign (e.g., non-self-antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade) cell-mediated immune responses (e.g., responses mediated by T-cells (e.g., antigen-specific T-cells) and non-specific cells of the immune system) and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an antigen (e.g., a pathogen) as well as acquired (e.g., memory) responses that are a result of an adaptive immune response).

As used herein, the term "immunity" refers to protection from disease (e.g., preventing or attenuating (e.g., suppression) of a sign, symptom or condition of the disease (e.g., tumor or cancer growth and/or metastasis) upon exposure an immunogen. Immunity can be innate (e.g., non-adaptive (e.g., non-acquired) immune responses that exist in the absence of a previous exposure to an immunogen) and/or acquired/adaptive (e.g., immune responses that are mediated by T and/or B cells following a previous exposure to immunogen (e.g., that exhibit increased specificity and reactivity to the immunogen).

"Immunocompetence" refers to the capacity to respond immunologically to an antigen or immunogen.

The term "immunogen" as used herein refers to an agent or substance capable of eliciting an immune response or producing immunity. When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual.

The term "immunotherapy" refers to any therapy in which one or more components of a human's or animal's immune system is deliberately modulated in order to directly or indirectly achieve some therapeutic benefit, including systemic and/or local effects, and preventative and/or curative effects. Immunotherapy can involve administering one or more immunotherapeutic agents, either alone or in any combination, to a human or animal subject by any route (e.g., orally, intravenously, dermally, by injection, by inhalation, etc.), whether systemically, locally or both. Immunotherapy can involve provoking, increasing, decreasing, halting, preventing, blocking or otherwise modulating the production of cytokines, and/or activating or deactivating cytokines or immune cells, and/or modulating the levels of immune cells, and/or delivering one or more therapeutic or diagnostic substances to a particular location in the body or to a particular type of cell or tissue, and/or destroying particular cells or tissue. Immunotherapy can be used to achieve local effects, systemic effects or a combination of both.

The term "immunotherapeutic agent" as used herein refers to any agent, compound, or biologic that indirectly or directly restores, enhances, stimulates or increases the body's immune response against cancer cells and/or that decreases the side effects of other anticancer therapies. Immunotherapy is thus a therapy that directly or indirectly stimulates or enhances the immune system's responses to cancer cells and/or lessens the side effects that may have been caused by other anti-cancer agents. Immunotherapy is also referred to in the art as immunologic therapy, biological therapy biological response modifier therapy and biotherapy. Examples of common immunotherapeutic agents known in the art include, but are not limited to, cytokines, cancer vaccines, monoclonal antibodies and non-cytokine adjuvants. Alternatively the immunotherapeutic treatment may consist of administering the subject with an amount of immune cells (T-cells, NK, cells, DCs, B-cells, etc.). Immunotherapeutic agents can be non-specific, i.e., boost the immune system generally so that the human body becomes more effective in fighting the growth and/or spread of cancer cells, or they can be specific, i.e., targeted to the cancer cells themselves. Immunotherapy regimens may combine the use of non-specific and specific immunotherapeutic agents. Non-specific immunotherapeutic agents are substances that stimulate or indirectly improve the immune system. Non-specific immunotherapeutic agents have been used alone as a main therapy for the treatment of cancer, as well as in addition to a main therapy, in which case the non-specific immunotherapeutic agent functions as an adjuvant to enhance the effectiveness of other therapies (e.g., cancer vaccines). Non-specific immunotherapeutic agents can also function in this latter context to reduce the side effects of other therapies, for example, bone marrow suppression induced by certain chemotherapeutic agents. Non-specific immunotherapeutic agents can act on key immune system cells and cause secondary responses, such as increased production of cytokines and immunoglobulins. Alternatively, the agents can themselves comprise cytokines. Non-specific immunotherapeutic agents are generally classified as cytokines or non-cytokine adjuvants. A number of cytokines have found application in the treatment of cancer either as general non-specific immunotherapies designed to boost the immune system, or as adjuvants provided with other therapies. Suitable cytokines include, but are not limited to, interferons, interleukins and colony-stimulating factors. Interferons (IFNs) contemplated by the present disclosure include the common types of IFNs, IFN-alpha (IFN-α), IFN-beta (IFN-β) and IFN-gamma (IFN-γ). IFNs can act directly on cancer cells, for example, by slowing their growth, promoting their development into cells with more normal behavior and/or increasing their production of antigens thus making the cancer cells easier for the immune system to recognize and destroy. IFNs can also act indirectly on cancer cells, for example, by slowing down angiogenesis, boosting the immune system and/or stimulating natural killer (NK) cells, T-cells and macrophages. Recombinant IFN-alpha is available commercially as Roferon (Roche Pharmaceuticals) and Intron A (Schering Corporation). Interleukins contemplated by the present disclosure include IL-2, IL-4, IL-11 and IL-12. Examples of commercially available recombinant interleukins include Proleukin® (IL-2; Chiron Corporation) and Neumega® (IL-12; Wyeth Pharmaceuticals). Zymogenetics, Inc. (Seattle, Wash.) is currently testing a recombinant form of IL-21, which is also contemplated for use in the combinations of the present disclosure. Colony-stimulating factors (CSFs) contemplated by the present disclosure include granulocyte colony stimulating factor (G-CSF or filgrastim), granulocyte-macrophage colony stimulating factor (GM-CSF or sargramostim) and erythropoietin (epoetin alfa, darbopoietin). Treatment with one or more growth factors can help to stimulate the generation of new blood cells in subjects undergoing traditional chemotherapy. Accordingly, treatment with CSFs can be helpful in decreasing the side effects associated with chemotherapy and can allow for higher doses of chemotherapeutic agents to be used. Various-recombinant colony stimulating factors are available commercially, for example, Neupogen® (G-CSF; Amgen), Neulasta (pelfilgrastim; Amgen), Leukine (GM-CSF; Berlex), Procrit (erythropoietin; Ortho Biotech), Epogen (erythropoietin; Amgen), Aranesp (erythropoietin). In addition to having specific or non-specific targets, immunotherapeutic agents can be active, i.e., stimulate the body's own immune response including humoral and cellular immune responses, or they can be passive, i.e., comprise immune system components such as antibodies, effector immune cells, antigen-presenting cells etc. that were generated external to the body. In specific embodiments, passive immunotherapy involves the use of one or more monoclonal antibodies that are specific for a particular antigen found on the surface of a cancer cell or immune cell or that are specific for a particular cell growth factor. Monoclonal antibodies may be used in the treatment of cancer in a number of ways, for example, to enhance a subject's immune response to a specific type of cancer, to interfere with the growth of cancer cells by targeting specific cell growth factors, such as those involved in angiogenesis, or by enhancing the delivery of other anticancer agents to cancer cells when linked or conjugated to agents such as chemotherapeutic agents, radioactive particles or toxins. Monoclonal antibodies currently used as cancer immunotherapeutic agents include, but are not limited to, alemtuzumab (LEMTRADA®), bevacizumab (AVASTIN®), cetuximab (ERBITUX®), panitumumab (VECTIBIX®), pertuzumab (OMNITARG®, 2C4), trastuzumab (HERCEPTIN®), tositumomab (Bexxar®), abciximab (REOPRO®), adalimumab (HUMIRA®), apolizumab, aselizumab, atlizumab, bapineuzumab, basiliximab (SIMULECT®), bavituximab, belimumab (BENLYSTA®) briankinumab, canakinumab (ILARIS®), cedelizumab, certolizumab pegol (CIMZIA®), cidfusituzumab, cidtuzumab, cixutumumab, clazakizumab, crenezumab, daclizumab (ZENAPAX®), dalotuzumab, denosumab (PROLIA®, XGEVA®), eculizumab (SOLIRIS®), efalizumab, epratuzumab, erlizumab, felvizumab, fontolizumab, golimumab (SIMPONI®), ipilimumab, imgatuzumab, infliximab (REMICADE®), labetuzumab, lebrikizumab, lexatumumab, lintuzumab, lucatumumab, lulizumab pegol, lumretuzumab, mapatumumab, matuzumab, mepolizumab, mogamulizumab, motavizumab, motovizumab, muronomab, natalizumab (TYSABRI®), necitumumab (PORTRAZZA®), nimotuzumab (THERACIM®), nolovizumab, numavizumab, olokizumab, omalizumab (XOLAIR®), onartuzumab (also known as MetMAb), palivizumab (SYNAGIS®), pascolizumab, pecfusituzumab, pectuzumab, pembrolizumab (KEYTRUDA®), pexelizumab, priliximab, ralvizumab, ranibizumab, (LUCENTIS®), reslivizumab, reslizumab, resyvizumab, robatumumab, rontalizumab, rovelizumab, ruplizmnab, sarilumab, secukinumab, seribantumab, sifalimumab, sibrotuzumab, siltuximab (SYLVANT®) siplizumab, sontuzumab, tadocizumab, talizumab, tefibazumab, tocilizumab (ACTEMRA®), toralizumab, tucusituzumab, umavizmab, urtoxazumab, ustekinumab (STELARA®), vedolizumab (ENTYVIO®), visilizumab, zanolimumab, zalutumumab. In specific embodiments, the immunotherapy comprises a T-cell therapy, representative examples of which include adoptive T-cell therapy, tumor-infiltrating lymphocyte (TIL) immunotherapy, autologous cell therapy, engineered autologous cell therapy, and allogeneic T-cell transplantation. Non-limiting examples of T-cell therapies are described in U.S. Patent Publication Nos. 2014/0154228 and 2002/0006409, U.S. Pat. No. 5,728,388, and International Publication No. WO 2008/081035. The T-cells of the immunotherapy can come from any source known in the art. For example, T-cells can be differentiated in vitro from a hematopoietic stem cell population, or T-cells can be obtained from a subject. T-cells can be obtained from, e.g., peripheral blood mononuclear cells, bone marrow, lymph node tissue, cord blood, thymus tissue, tissue from a site of infection, ascites, pleural effusion, spleen tissue, and tumors, combination thereof. Alternatively, or in addition, the T-cells can be derived from one or more T-cell lines available in the art. T-cells can also be obtained from a unit of blood collected from a subject using any number of techniques known to the skilled artisan, such as FICOLL™ separation and/or apheresis. Additional methods of isolating T-cells for T-cell therapy are disclosed in U.S. Patent Publication No. 2013/0287748.

As used herein, the term "increase" or "increased' with reference to a biomarker or biomarker complex level refers to a statistically significant and measurable increase in the biomarker or biomarker complex level compared to the level of another biomarker or biomarker complex or to a control level. The increase is preferably an increase of at least about 10%, or an increase of at least about 20%, or an increase of at least about 30%, or an increase of at least about 40%, or an increase of at least about 50%.

The term "infection" refers to invasion of body tissues by disease-causing microorganisms, their multiplication and the reaction of body tissues to these microorganisms and the toxins they produce. "Infection" includes but are not limited to infections by viruses, prions, bacteria, viroids, parasites, protozoans and fungi. Non-limiting examples of viruses include Retroviridae human immunodeficiency viruses, such as HIV-1 (also referred to as HTLV-III, LAV or HTLV-III/LAV, or HIV-III); and other isolates, such as HIV-LP); Picornaviridae (e.g., polio viruses, hepatitis A virus; enteroviruses, human Coxsackie viruses, rhinoviruses, echoviruses); Calciviridae (e.g., strains that cause gastroenteritis, including Norwalk and related viruses); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus, Metapneumovirus); Orthomyxoviridae (e.g., influenza viruses); Bunyaviridae (e.g., Hantaan viruses, bunya viruses, phieboviruses and Nairo viruses); Arenaviridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxviridae (variola viruses, VACV, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); and astroviruses. Representative bacteria that are known to be pathogenic include pathogenic *Pasteurella* species (e.g., *Pasteurella multocida*), *Staphylococcus* species (e.g., *Staphylococcus aureus*), *Streptococcus* species (e.g., *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic sps.), *Streptococcus pneumoniae*), *Neisseria* species (e.g., *Neisseria gonorrhoeae*, *Neisseria meningitidis*), *Escherichia* species (e.g., enterotoxigenic *E. coli* (ETEC), enteropathogenic *E. coli* (EPEC), enterohemorrhagic *E. coli* (EHEC), and enteroinvasive *E. coli* (EIEC)), *Bordetella* species, *Campylobacter* species, *Legionella* species (e.g., *Legionella pneumophila*), *Pseudomonas* species, *Shigella* species, *Vibrio* species, *Yersinia* species, *Salmonella* species, *Haemophilus* species (e.g., *Haemophilus influenzae*), *Brucella* species, *Francisella* species, *Bacteroides* species, *Clostridiium* species (e.g., *Clostridium difficile*, *Clostridium perfringens*, *Clostridium tetani*), *Mycobacteria* species (e.g., *M. tuberculosis*, *M. avium*, *M. intracellulare*, *M. kansaii*, *M. gordonae*), *Helicobacter pyloris*, *Borelia burgdorferi*, *Listeria monocytogenes*, *Chlamydia trachomatis*, *Enterococcus* species, *Bacillus anthracis*, *Corynebacterium diphtheriae*, *Erysipelothrix rhusiopathiae*, *Enterobacter aerogenes*, *Klebsiella pneumoniae*, *Fusobacterium nucleatum*, *Streptobacillus moniliformis*, *Treponema pallidium*, *Treponema pertenue*, *Leptospira*, *Rickettsia*, and *Actinomyces israeli*. Non-limiting pathogenic fungi include *Cryptococcus neoformans*, *Histoplasma capsulatum*, *Coccidioides immitis*, *Blastomyces dermatitidis*, *Candida albicans*, *Candida glabrata*, *Aspergillus fumigata*, *Aspergillus flavus*, and *Sporothrix schenckii*. Illustrative pathogenic protozoa, helminths, *Plasmodium*, such as *Plasmodium falciparum*, *Plasmodium malariae*, *Plasmodium ovale*, and *Plasmodium vivax*; *Toxoplasma gondii*; *Trypanosoma brucei*, *Trypanosoma cruzi*; *Schistosoma haematobium*, *Schistosoma mansoni*, *Schistosoma japonicum*; *Leishmania donovani*; *Giardia intestinalis*; *Cryptosporidium parvum*; and the like.

As used herein, "instructional material" includes a publication, a recording, a diagram, or any other medium of expression which can be used to communicate the usefulness of the compositions and methods of the disclosure. The instructional material of the kit of the disclosure may, for example, be affixed to a container which contains the therapeutic or diagnostic agents of the disclosure or be shipped together with a container which contains the therapeutic or diagnostic and/or prognostic agents of the disclosure.

The term "label" when used herein refers to a detectable compound or composition. The label is typically conjugated or fused directly or indirectly to a reagent, such as a polynucleotide probe or an antibody, and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which results in a detectable product.

The term "leukocytes" or "white blood cell" as used herein refers to any immune cell, including monocytes, neutrophils, eosinophils, basophils, and lymphocytes.

The term "lymphocytes" as used herein refers to cells of the immune system which are a type of white blood cell. Lymphocytes include, but are not limited to, T-cells (cytotoxic and helper T-cells), B-cells and natural killer cells (NK cells). The term "tumor infiltrating lymphocyte" as used herein refers to lymphocytes that are present in a solid tumor. The term "circulating lymphocyte" as used herein refers to lymphocytes that are present in the circulation (e.g., present in blood).

As used herein, the term "localize" and its grammatical equivalents mean to accumulate in, or be restricted to, a specific or limited space or area, for example a specific cell, tissue, organelle, or intracellular region such as a cellular component (e.g., nucleus, cytoplasm, nuclear membrane, plasma membrane, etc.).

As used herein, the term "lower" with reference to a biomarker or biomarker complex measurement refers to a statistically significant and measurable difference in the level of a biomarker or biomarker complex measurement compared to the level of another biomarker or biomarker complex or to a control level where the biomarker or biomarker complex measurement is less than the level of the other biomarker or biomarker complex or the control level. The difference is preferably at least about 10%, or at least about 20%, or of at least about 30%, or of at least about 40%, or at least about 50%.

By "memory T effector cells" is meant a subset of T-cells including CTL and helper T-cells that have previously encountered and responded to their cognate antigen; thus, the term antigen-experienced T-cell is often applied. Such T-cells can recognize foreign microbes, such as bacteria or viruses, as well as cancer cells. Memory T effector cells have become "experienced" by having encountered antigen during a prior infection, encounter with cancer, or previous vaccination. At a second encounter with the microbe, memory T effector cells can reproduce to mount a faster and stronger immune response than the first time the immune system responded to the microbe. This behavior is utilized in T lymphocyte proliferation assays, which can reveal exposure to specific antigens.

By "obtained" is meant to come into possession. Samples so obtained include, for example, polypeptide extracts isolated or derived from a particular source, including cell lysates. For instance, the extract may be isolated directly from a biological fluid or tissue of a subject.

The terms "patient", "subject", "host" or "individual" used interchangeably herein, refer to any subject, particularly a vertebrate subject, and even more particularly a mammalian subject, for whom therapy or prophylaxis is desired. Suitable vertebrate animals that fall within the scope of the disclosure include, but are not restricted to, any member of the subphylum Chordata including primates (e.g., humans, monkeys and apes, and includes species of monkeys such from the genus *Macaca* (e.g., cynomologus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. A preferred subject is a human in need of a therapy and/or the analytical/determination methods of the present disclosure. However, it will be understood that the aforementioned terms do not imply that symptoms are present.

The term "pharmaceutical composition" or "pharmaceutical formulation" refers to a preparation which is in such form as to permit the biological activity of the active ingredient(s) to be effective, and which contains no additional components which are unacceptably toxic to a subject to which the composition or formulation would be administered. Such formulations are sterile. "Pharmaceutically acceptable" excipients (vehicles, additives) are those which can reasonably be administered to a subject mammal to provide an effective dose of the active ingredient employed.

As used herein, the term "PD-1" refers to any form of PD-1 and variants thereof that retain at least part of the activity of PD-1. Unless indicated differently, such as by specific reference to human PD-1, PD-1 includes all mammalian species of native sequence PD-1, e.g., human, canine, feline, equine, and bovine. One exemplary human PD-1 is found as UniProt Accession Number Q15116.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In some embodiments, a PD-1 binding antagonist reduces the negative co-stimulatory signal mediated by or through cell surface proteins expressed on T-cells mediated through PD-1 so as to render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab). In another specific aspect, a PD-1 binding antagonist is MK-3475 (pembrolizumab). In another specific aspect, a PD-1 binding antagonist is CT-011 (pidilizumab). In still another specific aspect, a PD-1 binding antagonist is AMP-224.

As used herein, "PD-L1" refers to the protein also known as "programmed cell death ligand 1," "cluster of differentiation 274 (i.e., CD274)" or "B7 homolog 1 (i.e., B7-H1)". The native protein comprises two extracellular domains, a transmembrane domain, and a cytoplasmic domain. The term encompasses full-length and/or unprocessed PD-L1 as well as any intermediate resulting from processing in the cell. PD-L1 can exist as a transmembrane protein or as a soluble protein; thus, the term as used herein may refer to the full-length or the extracellular domain of the protein. The term also encompasses naturally occurring variants of PD-L1, e.g., splice variants or allelic variants. The protein may additionally contain a tag, such as a his tag or Fc tag. The amino acid sequence of exemplary human full-length PD-L1 protein can e.g., be found under NCBI protein database accession number NP_054862.

"PD-L2" refers to the protein also known as "programmed cell death 1 ligand 2", "B7-DC", or "CD273" (cluster of differentiation 273). The term as used herein encompasses full-length and/or unprocessed PD-L2 as well as any intermediate resulting from processing in the cell. PD-L2 can exist as a transmembrane protein or as a soluble protein; thus, the term as used herein may refer to the full length or the extracellular domain of the protein. The term also encompasses naturally occurring variants of PD-L2, e.g., splice variants or allelic variants. The protein may additionally contain a tag, such as a his tag or Fc tag. The amino acid sequence of exemplary human full-length PD-L2 protein can e.g. be found under NCBI protein database accession number NP_079515.

The term "predictive" and grammatical forms thereof, generally refer to a biomarker or biomarker signature that provides a means of identifying, directly or indirectly, a likelihood of a patient responding to a therapy or obtaining a clinical outcome in response to therapy.

The term "prognostic" and grammatical forms thereof, generally refer to an agent or method that provides information regarding the likely progression or severity of a disease or condition in an individual. In some embodiments, prognosis also refers to the ability to demonstrate a positive or negative response to therapy or other treatment regimens, for the disease or condition in the subject. In some embodiments, prognosis refers to the ability to predict the presence or diminishment of disease/condition associated symptoms. A prognostic agent or method may comprise classifying a subject or sample obtained from a subject into one of multiple categories, wherein the categories correlate with different likelihoods that a subject will experience a particular outcome. For example, categories can be low risk and high risk, wherein subjects in the low risk category have a lower likelihood of experiencing a poor outcome (e.g., within a given time period such as 5 years or 10 years) than do subjects in the high risk category. A poor outcome could be, for example, disease progression, disease recurrence, or death attributable to the disease.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

As used herein, the term "reduce" or "reduced" with reference to a biomarker or biomarker complex level refers to a statistically significant and measurable reduction in the biomarker or biomarker complex level compared to the level of another biomarker or biomarker complex or to a control level. The reduction is preferably a reduction of at least about 10%, or a reduction of at least about 20%, or a reduction of at least about 30%, or a reduction of at least about 40%, or a reduction of at least about 50%.

As used herein, a cancer patient who has been treated with a therapy is considered to "respond", have a "response", have "a positive response" or be "responsive" to the therapy if the subject shows evidence of an anti-cancer effect according to an art-accepted set of objective criteria or reasonable modification thereof, including a clinically significant benefit, such as the prevention, or reduction of severity, of symptoms, or a slowing of the progression of the cancer. It will be understood that the aforementioned terms may also be used in regard to the cancer. A variety of different objective criteria for assessing the effect of anti-cancer treatments on cancers are known in the art. The World Health Organization (WHO) criteria (Miller, A B, et al., *Cancer* 1981; 47(1):207-14) and modified versions thereof, the Response Evaluation Criteria in Solid Tumors (RECIST) (Therasse P, et al., *J Natl Cancer Inst* 2000; 92:205-16), and revised version thereof (Eisenhauer E A, New response evaluation criteria in solid tumors: revised RECIST guideline (version 1.1). *Eur J Cancer* 2009; 45(2):228-47) are sets of objective criteria, based on imaging measurements of the size and number of tumor lesions and detection of new lesions, e.g., from computed tomography (CT), magnetic resonance imaging (MRI), or conventional radiographs. Dimensions of selected lesions (referred to as target lesions) are used to calculate the change in tumor burden between images from different time points. The calculated response is then categorized as complete response (CR), partial response (PR), stable disease (SD), or progressive disease (PD). CR is complete disappearance of tumor (−100%), and PD is an increase of about 20%-25% or greater (depending on the particular criteria) and/or the appearance of new lesions. PR is a significant reduction (of at least about 30%) in size of tumor lesions (without emergence of new lesions) but less than a complete response. SD is in between PR and PD. (See Tables 1 and 2 for details.) These criteria are widely used as a primary endpoint in Phase II trials evaluating the efficacy of anti-cancer agents, e.g., as a surrogate for overall survival. However, anatomic imaging alone using WHO, RECIST, and RECIST 1.1 criteria were designed to detect early effects of cytotoxic agents and have certain limitations, particularly in assessing the activity of newer cancer therapies that stabilize disease. Clinical response patterns in patients treated with immunotherapeutic anti-cancer agents or molecularly targeted anti-cancer agents may extend beyond those of cytotoxic agents and can manifest after an initial increase in tumor burden or the appearance of new lesions. For example, meaningful tumor responses to immune checkpoint inhibitor may occur after a delay, in some cases following WHO- or RECIST-defined PD. Criteria designated immune-related response criteria (irRC) were defined in an attempt to capture additional favorable response patterns observed with immune therapies (Wolchok, J D, et al. (2009) Guidelines for the evaluation of immune therapy activity in solid tumors: immune-related response criteria. *Clin. Care Res.* 15, 7412-7420.). Four patterns associated with favorable survival were identified, i.e., decreased baseline lesions without new lesions; durable stable disease; initial increase in total tumor burden but eventual response; and a reduction in total tumor burden during or after the appearance of new lesion(s), of which the latter two are distinct from the response patterns considered favorable according to WHO or RECIST criteria. The irRC include criteria for complete response (irCR), partial response (irPR), stable disease (irSD), and progressive disease (irPD). Among other things, the irRC incorporates measurable new lesions into "total tumor burden" and compares this variable to baseline measurements rather than assuming that new lesions necessarily represent progressive disease. In summary, according to the immune-related response criteria, irCR is complete disappearance of all lesions whether measurable or not, and no new lesions; irPR is a decrease in tumor burden ≥50% relative to baseline; irSD is disease not meeting criteria for irCR or irPR, in absence of it progressive disease (irPD); irPD is an increase in tumor burden .gtoreq.25% relative to nadir (the minimum recorded tumor burden) (Wolchok, supra). irCR, irPR and irPD require confirmation by a repeat, consecutive assessment at least 4 weeks from the date of first documentation. irCR, irPR, and irSD include all patients with CR, PR, or SD by WHO criteria as well as those patients that shift to these irRC categories from WHO PD. However, some patients who would be classified as having PD according to WHO or RECIST criteria are instead classified as having PR or SD according to the irRC, identifying them as likely to have favorable survival. The irRC are applicable to immune checkpoint inhibitors and other immunotherapeutic agents. One of ordinary skill in the art will appreciate that additional response criteria are known in the art, which take into consideration various factors such as changes in the degree of tumor arterial enhancement and/or tumor density as indicators of tumor viable tissue, with decreased arterial enhancement and decreased tumor density being indicators of reduced viable tumor tissue (e.g., due to tumor necrosis). For example, modified RECIST criteria (mRECIST) take into consideration changes in the degree of tumor arterial enhancement (Lencioni R and Llovet J M. Semin Liver Dis 30: 52-60, 2010). Choi criteria and modified Choi criteria take into consideration decrease in tumor density on CT. Choi H, et al., *J Clin Oncol* 25: 1753-1759, 2007; Nathan P D, et al., *Cancer Biol Ther* 9: 15-19, 2010; Smith A D, et al., *Am J Roentgenol* 194: 157-165, 2010. Such criteria may be particularly useful in certain cancer types and/or with certain classes of therapeutic agents. For example, changes in tumor size can be minimal in tumors such as lymphomas, sarcoma, hepatomas, mesothelioma, and gastrointestinal stromal tumor despite effective treatment. CT tumor density, contrast enhancement, or MRI characteristics appear more informative than size. In certain embodiments functional imaging, e.g., using positron emission tomography (PET) may be used. For example, PET response criteria in solid tumors (PERCIST) may be used, in which the treatment response is evaluated by metabolic changes assessed with (18)F-FDG PET imaging, with decreased uptake of the tracer being indicative of (Wahl R L, et al., *J Nucl Med* 2009; 50, Suppl 1:122S-50S). It will also be understood that response criteria developed for various specific cancer types such as melanoma, breast cancer and lung cancer, are known in the art. By contrast, a cancer patient who has been treated with a therapy is considered "not to respond", "to lack a response", to have "a negative response" or be "non-responsive" to the therapy if the therapy provides no clinically significant benefit, such as the prevention, or reduction of severity, of symptoms, or increases the rate of progression of the cancer.

For purposes of the present disclosure, a cancer patient treated with an immunotherapy (e.g., an immune checkpoint inhibitor) as monotherapy or in combination with one or more other active agents (e.g., a complement inhibitor, an additional anti-cancer agent, or both) is considered to "respond", have a "response", or be "responsive" to the treatment if the patient has a complete response, partial response, or stable disease according at least to the immune-related response criteria. (The cancer patient may also respond according to RECIST, RECIST 1.1, WHO, and/or other criteria such as those mentioned above.) Likewise, the cancer in such cases is said to "respond", be "responsive", or be "sensitive" to the treatment. The cancer patient is considered to "not respond", not have a "response", or to be "nonresponsive" to the treatment if the patient has progressive disease according to the immune-related response criteria. (The cancer patient may also not respond according to RECIST, RECIST 1.1, WHO, and/or other criteria such as those mentioned above). Likewise, the cancer in such cases said to "not respond", or to be "nonresponsive", "insensitive" or "resistant" to the treatment. (A cancer is also considered to have become resistant to treatment if it initially responds but the patient subsequently exhibits progressive disease in the presence of treatment.) Thus, for example, for methods and products described herein that relate to response to treatment for cancer (e.g., methods of predicting likelihood of response, methods of classifying patients according to predicted response, methods of increasing the likelihood of response) a response is defined as irCR, irPR, or irSD, and lack of response is defined as irPD unless otherwise specified. In certain embodiments any useful response criteria may be specified. The response criteria may have been shown to correlate with a benefit such as increased overall survival or other clinically significant benefit. It will be appreciated that refinements or revisions of existing response criteria that, e.g., encompass additional favorable patterns of clinical activity (e.g., correlating with increased overall survival) applicable to immune checkpoint inhibitors or are otherwise useful may be developed in the future. In certain embodiments any such response criteria may be specified for use in methods described herein.

The term "sample" as used herein includes any biological specimen that may be extracted, untreated, treated, diluted or concentrated from a subject. A sample includes within its scope a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample" as used herein encompasses materials removed from a subject or materials present in a subject.

A "reference sample", "reference cell", "reference tissue", "control sample", "control cell", or "control tissue", as used herein, refers to a sample, cell, tissue, standard, or level that is used for comparison purposes. In one embodiment, a reference sample, reference cell, reference tissue, control sample, control cell, or control tissue is obtained from a healthy and/or non-diseased part of the body (e.g., tissue or cells) of the same subject or individual. For example, healthy and/or non-diseased cells or tissue adjacent to the diseased cells or tissue (e.g., cells or tissue adjacent to a tumor). In another embodiment, a reference sample is obtained from an untreated tissue and/or cell of the body of the same subject or individual. In yet another embodiment, a reference sample, reference cell, reference tissue, control sample, control cell, or control tissue is obtained from a healthy and/or non-diseased part of the body (e.g., tissues or cells) of an individual who is not the subject or individual. In even another embodiment, a reference sample, reference cell, reference tissue, control sample, control cell, or control tissue is obtained from an untreated tissue and/or cell of the body of an individual who is not the subject or individual.

By "tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. The tissue sample may contain compounds which are not naturally intermixed with the tissue in nature such as preservatives, anticoagulants, buffers, fixatives, nutrients, antibiotics, or the like.

As used herein, the terms "stratifying" and "classifying" are used interchangeably herein to refer to sorting of subjects into different strata or classes based on the features of a particular physiological or pathophysiological state or condition. For example, stratifying a population of subjects according to whether they are likely to respond to a therapy (e.g., anti-infective therapy, cytotoxic therapy and/or immunotherapy) involves assigning the subjects based on levels of response to therapy biomarkers including PD-L2, in cancer cells optionally in combination with at least one histone polypeptide (e.g., an H2A polypeptide, an H2AX polypeptide and an H4 polypeptide).

"Sustained response" refers to the sustained effect on reducing infection or tumor growth after cessation of a treatment. For example, the extent of infection or tumor size may remain to be the same or smaller as compared to the extent or size at the beginning of the administration phase. In some embodiments, the sustained response has a duration at least the same as the treatment duration, at least 1.5×, 2.0×, 2.5×, or 3.0× length of the treatment duration.

A "T-cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T-cell dysfunctional disorders characterized by T-cell dysfunction include unresolved acute infection, chronic infection and tumor immunity.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with a cancer are mitigated or eliminated, including, but are not limited to, reducing the proliferation of (or destroying) cancerous cells, reducing pathogen infection, decreasing symptoms resulting from the disease, increasing the quality of life of those suffering from the disease, decreasing the dose of other medications required to treat the disease, and/or prolonging survival of individuals. The phrase "treatment with a therapy", "treating with a therapy", "treatment with an agent", "treating with an agent" and the like refers to the administration of an effective amount of a therapy or agent, including a cancer therapy or agent, (e.g., a cytotoxic agent or an immunotherapeutic agent) to a patient, or the concurrent administration of two or more therapies or agents, including cancer therapies or agents, (e.g., two or more agents selected from cytotoxic agents and immunotherapeutic agents) in effective amounts to a patient.

As used herein, "treatment outcome" refers to predicting the response of a cancer patient to a selected therapy or treatment, including the likelihood that a patient will experience a positive or negative outcome with a particular treatment. As used herein, "indicative of a positive treatment outcome" or the like refers to an increased likelihood that the patient will experience beneficial results from the selected treatment (e.g., complete or partial response, complete or partial remission, reduced tumor size, stable disease, etc.). By contrast, "indicative of a negative treatment outcome" or the like is intended to mean an increased likelihood that the patient will not benefit from the selected treatment with respect to the progression of the underlying cancer (e.g., progressive disease, disease recurrence, increased tumor size, etc.).

"Tumor," as used herein, refers to all neoplastic cell growth and proliferation, whether malignant or benign, and all pre-cancerous and cancerous cells and tissues. The terms "cancer", "cancerous", "cell proliferative disorder", "proliferative disorder" "hyperproliferative disorder" and "tumor" are not mutually exclusive as referred to herein.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

Each embodiment described herein is to be applied mutatis mutandis to each and every embodiment unless specifically stated otherwise.

2. Methods of Detection and Prognosis/Prediction

In accordance with the present disclosure, nuclear localization of PD-L2 can be employed as a biomarker of response to therapy (e.g., an anti-infective therapy, cytotoxic therapy and/or immunotherapy), disease status (e.g., severity or progression of disease) and/or immune status (e.g., immune function including T-cell function and antigen-presenting cell function). In specific embodiments, nuclear localization of PD-L2 is determined by detecting co-localization of PD-L2 with a histone polypeptide (e.g., an H2A polypeptide, an H2AX polypeptide or an H4 polypeptide). Nuclear localization of PD-L2 is suitably assessed in PD-L2-expressing cells such as but not limited to antigen-presenting cells (e.g., DC), immune effector cells such as B-cells and T-cells, and tumor cells. Representative PD-L2-expressing cell-containing patient samples include tissue samples such as solid tumors and fluid samples such as peripheral blood. In some embodiments, the sample is obtained prior to treatment with a therapy. In some embodiments, the tissue sample is formalin fixed and paraffin embedded, archival, fresh or frozen. In some embodiments, the sample is whole blood. In some embodiments, the whole blood comprises immune cells (e.g., APCs such as DCs and immune effector cells such as B-cells and T-cells), circulating tumor cells and any combinations thereof.

Presence and/or level/amount of a biomarker (e.g., PD-L2 (e.g., nuclear PD-L2, extranuclear PD-L2, etc.), or a complex comprising PD-L2 and a histone polypeptide (e.g., an H2A polypeptide, an H2AX polypeptide or an H4 polypeptide) pf the present disclosure, also referred to herein collectively as "response-to-therapy biomarkers" or "RTT biomarkers") at a cellular location (e.g., surface, cytoplasm or nucleus) can be determined qualitatively and/or quantitatively based on any suitable criterion known in the art. In certain embodiments, presence and/or level/amount of an RTT biomarker at a cellular location in a first sample is increased or elevated as compared to presence/absence and/or level/amount at the cellular location in a second sample. In certain embodiments, presence/absence and/or level/amount of an RTT biomarker at a cellular location in a first sample is decreased or reduced as compared to presence and/or expression level/amount at the cellular location in a second sample.

In some embodiments of any of the methods, an elevated or higher level/amount refers to an overall increase of about any of 10%, 20%, 30%, 40%, 50%, 60%, 70%, 80%, 90%, 95%, 96%, 97%, 98%, 99% or greater, in the level/amount of an RTT biomarker at a cellular location, as detected for example by standard art known methods such as those described herein, as compared to the level/amount of the RTT biomarker at the cellular location in a reference sample, reference cell, reference tissue, control sample, control cell, or control tissue. In certain embodiments, the elevated or higher level/amount refers to an increase in level/amount of an RTT biomarker at the sample cellular location wherein the increase is at least about any of 1.2×, 1.3×, 1.4×, 1.5×, 1.75×, 2×, 3×, 4×, 5×, 6×, 7×, 8×, 9×, 10×, 25×, 50×, 75×, or 100× the level/amount of the RTT biomarker at the cellular location in a reference sample, reference cell, reference tissue, control sample, control cell, or control tissue. In some embodiments, an elevated or higher level/amount refers to an overall increase at a cellular location of greater than about 1.5-fold, about 1.75-fold, about-2 fold, about 2.25-fold, about 2.5-fold, about 2.75-fold, about 3.0-fold, or about 3.25-fold as compared to the cellular location in a reference sample, reference cell, reference tissue, control sample, control cell, control tissue, or internal control.

In some embodiments of any of the methods, an elevated or higher level/amount refers to a ratio of the level/amount of an RTT biomarker at a first cellular location (e.g., nuclear PD-L2) to the level/amount of the RTT biomarker at a second cellular location (e.g., extranuclear PD-L2, cytoplasmic PD-L2, plasma membrane PD-L2, etc.), wherein the ratio is greater than any of about 0.55, 0.60, 0.65, 0.70, 0.75, 0.85, 0.90 or 0.95.

In some embodiments of any of the methods, an elevated or higher level/amount refers to higher level of an RTT biomarker in more than any of about 30%, 35%, 40%, 45%, 50%, 55%, 60%, 65%, 70%, 75%, 80%, 85%, 90%, or 95% of a patient's cells.

In some embodiments of any of the methods, a reduced or lower level/amount refers to an overall reduction of about any of 10%, 20%, 30%, 40%, 50%, 60%, 70%, 80%, 90%, 95%, 96%, 97%, 98%, 99% or greater, in the level of a RTT in a cellular location, as detected for example by standard art known methods such as those described herein, as compared to the level/amount in the cellular location in a reference sample, reference cell, reference tissue, control sample, control cell, or control tissue. In certain embodiments, a reduced or lower level/amount refers to a decrease in level/amount of a RTT biomarker in a cellular location in the sample wherein the decrease is at least about any of 0.9×, 0.8×, 0.7×, 0.6×, 0.5×, 0.4×, 0.3×, 0.2×, 0.1×, 0.05×, or 0.01× the level/amount of the RTT biomarker in the cellular location in a reference sample, reference cell, reference tissue, control sample, control cell, or control tissue.

Presence and/or level/amount of various RTT biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), proteomics.

According to some embodiments, presence and/or level/amount is measured by observing protein levels/amounts. In certain embodiments, the method comprises contacting the sample with an antibody to an RTT biomarker (e.g., anti-PD-L2 antibody), optionally in combination with an antibody to at least one histone polypeptide (e.g., H2A polypeptide, an H2AX polypeptide and/or an H4 polypeptide) under conditions permissive for binding of the biomarker(s), and detecting whether a complex is formed between the antibody/antibodies and the biomarker(s). Such method may be an in vitro or in vivo method. In some embodiments, one or more anti-RTT biomarker antibodies are used to select subjects eligible for treatment with a therapy (e.g., anti-infective therapy, cytotoxic therapy and/or immunotherapy).

In certain embodiments, the presence and/or level/amount of biomarker proteins in a sample is examined using IHC and staining protocols. IHC staining of tissue sections has been shown to be a reliable method of determining or detecting presence or the level/amount of proteins in a sample, including the cellular localization of the proteins. In some embodiments, the level/amount of an RTT biomarker is determined using a method comprising: (a) performing IHC analysis of a sample (such as a tumor sample or a sample comprising immune cells, including APCs such as DCs) with an antibody; and b) determining the level/amount of the biomarker at a cellular location (e.g., nuclear, cytoplasm and/or plasma membrane) in the sample. In some embodiments, IHC staining intensity is determined relative to a reference. In some embodiments, the reference is a reference value. In some embodiments, the reference is a reference sample (e.g., control cell line staining sample or tissue sample from a non-cancerous patient or a patient lacking a pathogenic infection).

In some embodiments, the presence and/or level/amount of an RTT biomarker is evaluated on a tumor or tumor sample. As used herein, a tumor or tumor sample may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor associated intratumoral cells and/or tumor associated stroma may include areas of immune infiltrates (e.g., tumor infiltrating immune cells as described herein) immediately adjacent to and/or contiguous with the main tumor mass. In some embodiments, RTT biomarker expression is evaluated on tumor cells. In some embodiments, the presence and/or level/amount of an RTT biomarker is evaluated on immune cells (e.g., APCs such as DCs or T-cells), for example within the tumor area as described above, such as tumor infiltrating immune cells, or within biological fluid such as blood including peripheral blood.

In alternative methods, the sample may be contacted with an antibody specific for an RTT biomarker under conditions sufficient for an antibody-biomarker complex to form, and then detecting the complex. The presence or level/amount of the biomarker may be detected in a number of ways, such as by Western blotting and ELISA procedures for assaying a wide variety of tissues and samples, including plasma or serum. A wide range of immunoassay techniques using such an assay format are available, see, e.g., U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target biomarker.

In certain embodiments, the samples are normalized for both differences in the amount of the biomarker assayed and variability in the quality of the samples used, and variability between assay runs. Such normalization may be accomplished by detecting and incorporating the expression of certain normalizing biomarkers, including expression products of well-known housekeeping genes. Alternatively, normalization can be based on the mean or median signal of all of the assayed proteins or a large subset thereof (global normalization approach). On a protein-by-protein basis, measured normalized amount of a subject tumor protein is compared to the amount found in a reference set. Normalized levels for each protein per tested tumor per subject can be expressed as a percentage of the expression level measured in the reference set. The presence and/or level/amount measured in a particular patient sample to be analyzed will fall at some percentile within this range, which can be determined by methods well known in the art.

In some embodiments, the sample is a clinical sample. In other embodiments, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood. Proteins can be detected from cancer or tumor tissue or from other body samples such as urine, sputum, serum or plasma. Cancer cells may be sloughed off from cancer lesions and appear in such body samples. By screening such body samples, a simple early diagnosis can be achieved for these cancers. In addition, the response to a therapy can be monitored more easily by testing such body samples for RTT biomarkers.

The same techniques discussed above for detection of target proteins in cancerous samples can be applied to other body samples, including tissues and biological fluids associated with a pathogenic infection.

In certain embodiments, a reference sample, reference cell, reference tissue, control sample, control cell, or control tissue is a single sample or combined multiple samples from the same subject or individual that are obtained at one or more different time points than when the test sample is obtained. For example, a reference sample, reference cell, reference tissue, control sample, control cell, or control tissue is obtained at an earlier time point from the same subject or individual than when the test sample is obtained. Such reference sample, reference cell, reference tissue, control sample, control cell, or control tissue may be useful if the reference sample is obtained during initial diagnosis of cancer and the test sample is later obtained when the cancer becomes metastatic or resistant to treatment with a therapy.

In certain embodiments, a reference sample, reference cell, reference tissue, control sample, control cell, or control tissue is a combination of multiple samples from one or more healthy individuals who are not the subject or individual. In certain embodiments, a reference sample, reference cell, reference tissue, control sample, control cell, or control tissue is a combination of multiple samples from one or more individuals with a disease (e.g., cancer or pathogenic infection) who are not the subject or individual. In certain embodiments, a reference sample, reference cell, reference tissue, control sample, control cell, or control tissue is pooled samples from normal tissues or biological fluids such as blood from one or more individuals who are not the subject or individual. In certain embodiments, a reference sample, reference cell, reference tissue, control sample, control cell, or control tissue is pooled samples from tumor tissues or pooled blood samples from one or more individuals with a disease (e.g., cancer or a pathogenic infection) who are not the subject or individual.

In some embodiments, the sample is a tissue sample from the individual. In some embodiments, the tissue sample is a tumor tissue sample (e.g., biopsy tissue). In some embodiments, the tissue sample is lung tissue. In some embodiments, the tissue sample is renal tissue. In some embodiments, the tissue sample is skin tissue. In some embodiments, the tissue sample is pancreatic tissue. In some embodiments, the tissue sample is gastric tissue. In some embodiments, the tissue sample is bladder tissue. In some embodiments, the tissue sample is esophageal tissue. In some embodiments, the tissue sample is mesothelial tissue. In some embodiments, the tissue sample is breast tissue. In some embodiments, the tissue sample is thyroid tissue. In some embodiments, the tissue sample is colorectal tissue. In some embodiments, the tissue sample is head and neck tissue. In some embodiments, the tissue sample is osteosarcoma tissue. In some embodiments, the tissue sample is prostate tissue. In some embodiments, the tissue sample is ovarian tissue, HCC (liver), blood cells, lymph nodes, and/or bone/bone marrow tissue. In some embodiments, the tissue sample is colon tissue. In some embodiments, the tissue sample is endometrial tissue. In some embodiments, the tissue sample is brain tissue (e.g., glioblastoma, neuroblastoma, and so forth).

In some embodiments, a tumor tissue sample (the term "tumor sample" is used interchangeably herein) may encompass part or all of the tumor area occupied by tumor cells. In some embodiments, a tumor or tumor sample may further encompass tumor area occupied by tumor associated intratumoral cells and/or tumor associated stroma (e.g., contiguous peri-tumoral desmoplastic stroma). Tumor associated intratumoral cells and/or tumor associated stroma may include areas of immune infiltrates (e.g., tumor infiltrating immune cells as described herein) immediately adjacent to and/or contiguous with the main tumor mass.

In some embodiments, tumor cell staining is expressed as the percentage of all tumor cells showing nuclear staining of any intensity. Infiltrating immune cell staining may be expressed as the percent of the total tumor area occupied by immune cells that show staining of any intensity. The total tumor area encompasses the malignant cells as well as tumor-associated stroma, including areas of immune infiltrates immediately adjacent to and contiguous with the main tumor mass. In addition, infiltrating immune cell staining may be expressed as the percent of all tumor infiltrating immune cells.

In some embodiments, immune cell staining (e.g., staining of APCs such as DCs, or immune effector cells such as B-cells and/or T-cells,) is expressed as the percentage of all immune cells showing nuclear staining of any intensity.

In some embodiments of any of the methods, the disease is a tumor. In some embodiments, the tumor is a malignant cancerous tumor (i.e., cancer). In some embodiments, the tumor and/or cancer is a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, prolymphocytic leukemia, or hairy cell leukemia) or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further divided into those of epithelial cell origin and those of non-epithelial cell origin. Examples of epithelial cell solid tumors include tumors of the gastrointestinal tract, colon, colorectal (e.g., basaloid colorectal carcinoma), breast, prostate, lung, kidney, liver, pancreas, ovary (e.g., endometrioid ovarian carcinoma), head and neck, oral cavity, stomach, duodenum, small intestine, large intestine, anus, gall bladder, labium, nasopharynx, skin, uterus, male genital organ, urinary organs (e.g., urothelial carcinoma, dysplastic urothelial carcinoma, transitional cell carcinoma), bladder, and skin. Solid tumors of non-epithelial origin include sarcomas, brain tumors, and bone tumors. In some embodiments, the cancer is non-small cell lung cancer (NSCLC). In some embodiments, the cancer is second-line or third-line locally advanced or metastatic non-small cell lung cancer. In some embodiments, the cancer is adenocarcinoma. In some embodiments, the cancer is squamous cell carcinoma. In some embodiments, the cancer is non-small cell lung cancer (NSCLC), glioblastoma, neuroblastoma, melanoma, breast carcinoma (e.g. triple-negative breast cancer), gastric cancer, colorectal cancer (CRC), or hepatocellular carcinoma. In some embodiments, the cancer is a primary tumor. In some embodiments, the cancer is a metastatic tumor at a second site derived from any of the above types of cancer.

In some embodiments of any of the methods, the disease is an infectious disease (i.e., a diseased caused by a pathogenic infection). The infection may be chronic or acute and suitably results from a pathogen selected from bacteria, virus, fungi and protozoan. Illustrative diseases caused by bacteria may optionally comprise one or more of sepsis, septic shock, sinusitis, skin infections, pneumonia, bronchitis, meningitis, bacterial vaginosis, urinary tract infection (UTI), bacterial gastroenteritis, impetigo and erysipelas, erysipelas, cellulitis, anthrax, whooping cough, Lyme disease, brucellosis, enteritis, acute enteritis, tetanus, diphtheria, pseudomembranous colitis, gas gangrene, acute food poisoning, anaerobic cellulitis, nosocomial infections, diarrhea, meningitis in infants, traveler's diarrhea, hemorrhagic colitis, hemolytic-uremic syndrome, tularemia, peptic ulcer, gastric and duodenal ulcers, legionnaire's disease, Pontiac fever, leptospirosis, listeriosis, leprosy (Hansen's disease), tuberculosis, gonorrhea, ophthalmia neonatorum, septic arthritis, meningococcal disease including meningitis, waterhouse-friderichsen syndrome, pseudomonas infection, rocky mountain spotted fever, typhoid fever type salmonellosis, salmonellosis with gastroenteritis and enterocolitis, bacillary dysentery/shigellosis, coagulase-positive staphylococcal infections: localized skin infections including diffuse skin infection (impetigo), deep localized infections, acute infective endocarditis, septicemia, necrotizing pneumonia, toxinoses such as toxic shock syndrome and staphylococcal food poisoning, cystitis, endometritis, otitis media, streptococcal pharyngitis, scarlet fever, rheumatic fever, puerperal fever, necrotizing fasciitis, cholera, plague (including bubonic plague and pneumonic plague), as well as any infection caused by a bacteria selected from but not limited to *Helicobacter pylori, Boreliai burgdorferi, Legionella pneumophilia, Mycobacteria* sp. (e.g., *M. tuberculosis, M. avium, M. intracellulare, M. kansaii, M. gordonae*), *Staphylococcus aureus, Neisseria gonorrhea, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sp.), *Streptococcus pneumoniae*, pathogenic *Campylobacter* sp., *Enterococcus* sp., *Haemophilus influenzae, Bacillus antracis, Corynebacterium diphtheriae, Corynebacterium* sp., *Erysipelothrix rhusiopathiae, Clostridium perfringers, Clostridium tetani, Enterobacter erogenes, Klebsiella pneuomiae, Pasteurella multicoda, Bacteroides* sp., *Fusobacterium nucleatum, Streptobacillus moniliformis, Treponema pallidium, Treponema pertenue, Leptospira*, and *Actinomyeces israelli*.

Non limiting examples of infectious diseases caused by virus are selected from acquired immune deficiency (AIDS), West Nile encephalitis, coronavirus infection, rhinovirus infection, influenza, dengue, hemorrhagic fever; an otological infection; severe acute respiratory syndrome (SARS), acute febrile pharyngitis, pharyngoconjunctival fever, epidemic keratoconjunctivitis, infantile gastroenteritis, infectious mononucleosis, Burkitt's lymphoma, acute hepatitis, chronic hepatitis, hepatic cirrhosis, hepatocellular carcinoma, primary HSV-1 infection, (gingivostomatitis in children, tonsillitis & pharyngitis in adults, keratoconjunctivitis), latent HSV-1 infection (herpes labialis, cold sores), aseptic meningitis, Cytomegalovirus infection, Cytomegalic inclusion disease, Kaposi sarcoma, Castleman disease, primary effusion lymphoma, influenza, measles, encephalitis, postinfectious encephalomyelitis, Mumps, hyperplastic epithelial lesions (common, flat, plantar and anogenital warts, laryngeal papillomas, epidermodysplasia verruciformis), croup, pneumonia, bronchiolitis, Poliomyelitis, Rabies, bronchiolitis, pneumonia, German measles, congenital rubella, Hemorrhagic Fever, Chickenpox, Dengue, Ebola infection, Echovirus infection, Epstein-Bar virus (EBV) infection, Fifth Disease, Filovirus, Flavivirus, Hand, foot & mouth disease, Herpes Zoster Virus (Shingles), Human Papilloma Virus Associated Epidermal Lesions, Lassa Fever, Lymphocytic choriomeningitis, Parainfluenza Virus infection, Paramyxovirus, Parvovirus B19 Infection, Picornavirus, Poxviruses infection, Rotavirus diarrhea, Rubella, Rubeola, Varicella, Variola infection.

Representative diseases caused by fungi includes allergic bronchopulmonary aspergillosis, aspergilloma, aspergillosis, basidiobolomycosis, blastomycosis, candidiasis, chronic pulmonary aspergillosis, chytridiomycosis, coccidioidomycosis, conidiobolomycosis, covered smut (barley), cryptococcosis, dermatophyte, dermatophytid, dermatophytosis, endothrix, entomopathogenic fungus, epizootic lymphangitis, epizootic ulcerative syndrome, esophageal candidiasis, exothrix, fungemia, histoplasmosis, lobomycosis, massospora cicadina, mycosis, mycosphaerella fragariae, myringomycosis, paracoccidioidomycosis, pathogenic fungi, penicilliosis, thousand cankers disease, tinea, zeaspora, zygomycosis.

Illustrative diseases caused by parasites include acanthamoeba, amoebiasis, ascariasis, ancylostomiasis, anisakiasis, babesiosis, balantidiasis, baylisascariasis, blastocystosis, candiru, chagas disease, clonorchiasis, cochliomyia, coccidia, chinese liver fluke cryptosporidiosis, dientamoebiasis, diphyllobothriasis, dioctophyme renalis infection, dracunculiasis, echinococcosis, elephantiasis, enterobiasis, fascioliasis, fasciolopsiasis, filariasis, giardiasis, gnathostomiasis, hymenolepiasis, halzoun syndrome, isosporiasis, katayama fever, leishmaniasis, lymphatic filariasis, malaria, metagonimiasis, myiasis, onchocerciasis, pediculosis, primary amoebic meningoencephalitis, parasitic pneumonia, paragonimiasis, scabies, schistosomiasis, sleeping sickness, strongyloidiasis, sparganosis, rhinosporidiosis, river blindness, taeniasis (cause of cysticercosis), toxocariasis, toxoplasmosis, trichinosis, trichomoniasis, trichuriasis, trypanosomiasis, tapeworm infection.

In specific embodiments, an infectious disease is a disease caused by any of hepatitis B, hepatitis C, infectious mononucleosis, EBV, cytomegalovirus, AIDS, HIV-1, HIV-2, tuberculosis, malaria and schistosomiasis.

In some embodiments, an RTT biomarker is detected in the sample using a method selected from the group consisting of FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, and combinations thereof. In some embodiments, the RTT biomarker is detected in blood samples. In some embodiments, the RTT biomarker is detected in circulating tumor cells in blood samples. In some embodiments, the RTT biomarker is detected in immune cells (e.g., immune effector cells, and APCs such as DCs). Any suitable method to isolate/enrich such population of cells may be used including, but not limited to, cell sorting. In some embodiments, the level/amount of nuclear PD-L2 is reduced in samples from individuals that respond to treatment with a therapy, suitably an immunotherapy (e.g., one that comprises an anti-immune checkpoint molecule antibody such as an anti-PD-1 antagonist antibody). In some embodiments, the level/amount of nuclear PD-L2 is elevated in samples from individuals that do not respond or respond weakly to treatment with a therapy, suitably an immunotherapy (e.g., one that comprises an anti-immune checkpoint molecule antibody such as an anti-PD-1 antagonist antibody). In some embodiments, the level/amount of extranuclear PD-L2 is reduced in samples from individuals that do not respond or weakly respond to treatment with a therapy, suitably an immunotherapy (e.g., one that comprises an anti-immune checkpoint molecule antibody such as an anti-PD-1 antagonist antibody). In some embodiments, the level/amount of extranuclear PD-L2 is elevated in samples from individuals that respond to treatment with a therapy, suitably an immunotherapy (e.g., one that comprises an anti-immune checkpoint molecule antibody such an anti-PD-1 antagonist antibody).

Also provided herein are predictive/prognostic methods and kits that are based on the determination that PD-L2 co-localizes in the nucleus with a nuclear binding partner of PD-L2 (e.g., a histone polypeptide representative examples of which include an H2A polypeptide, an H2AX polypeptide and an H4 polypeptide) and that this co-localization contributes at least in part to resistance or non-responsiveness to therapy (e.g., an anti-infective therapy, cytotoxic therapy and/or immunotherapy), disease status (e.g., severity or progression of disease) and/or immune status (e.g., immune function including T-cell function and antigen-presenting cell function). These methods suitably comprise: (i) obtaining a sample from a patient, wherein the sample comprises a PD-L2-expressing cell (e.g., a tumor cell or an immune cell inclusive of immune effector cells, and APCs such as DCs); (ii) contacting the sample with a first antigen-binding molecule that binds to PD-L2 in the sample and a second antigen-binding molecule that binds to the PD-L2-binding partner in the sample; and (iii) detecting localization of the first and second antigen-binding molecule(s) in the nucleus of the PD-L2-expressing cell, wherein localization of the first and second antigen-binding molecules in the nucleus of the PD-L2-expressing cell is indicative that the PD-L2-expressing cell has increased likelihood of resistance to the therapy, that the patient is a likely non-responder to the therapy, that the patient is selected for not treating with the therapy, and/or that the treatment outcome for the patient is predicted to be a likely negative treatment outcome.

Localization of PD-L2 and the nuclear binding partner of PD-L2 in the nucleus of a PD-L2-expressing cell may be performed using any suitable localization technique, e.g., by IHC, typically using an anti-PD-L2 antibody that has a different detectable moiety or label than an anti-PD-L2-binding partner antibody. In some embodiments, spatial proximity assays (also referred to as "proximity assays") are employed, which can be used to assess the formation of a complex between the PD-L2 and the nuclear binding partner of PD-L2. Proximity assays rely on the principle of "proximity probing", wherein an analyte, typically an antigen, is detected by the coincident binding of multiple (i.e., two or more, generally two, three or four) binding agents or probes, which when brought into proximity by binding to the analyte (hence "proximity probes") allow a signal to be generated.

In some embodiments, at least one of the proximity probes comprises a nucleic acid domain (or moiety) linked to the analyte-binding domain (or moiety) of the probe, and generation of the signal involves an interaction between the nucleic acid moieties and/or a further functional moiety which is carried by the other probe(s). Thus signal generation is dependent on an interaction between the probes (more particularly by the nucleic acid or other functional moieties/domains carried by them) and hence only occurs when both the necessary two (or more) probes have bound to the analyte, thereby lending improved specificity to the detection system. The concept of proximity probing has been developed in recent years and many assays based on this principle are now well-known in the art.

Proximity assays are typically used to assess whether two particular proteins or portions thereof are in close proximity, e.g., proteins that are bound to each other, fusion proteins, and/or proteins that are positioned in close proximity. One such assay, known as proximity ligation assay (PLA), and which is used in some embodiments of the present disclosure, features two antibodies (raised in different species) bound to the targets of interest (see, *Nature Methods* 3, 995-1000 (2006)). PLA probes, which are species-specific secondary antibodies with a unique oligonucleotide strand attached, are then bound to the appropriate primary antibodies. In the case of the targets being in close proximity, the oligonucleotide strands of the PLA probes can interact with additional ssDNA and DNA ligase such they can be circulated and amplified via rolling circle amplification (RCA). When highly processive DNA polymerases such as Phi29 DNA polymerase is used, the circular DNA template can be replicated hundreds to thousands of times longer and as a result producing ssDNA molecules from hundreds of nanometers to microns in length (see, *Angewandte Chemie* International Edition, 2008, 47, 6330-6337). After the amplification, the replicated DNA can be detected via detection systems. Thus, a visible signal is indicative that the targets of interest are in close proximity. These assays feature the use of several DNA-antibody conjugates as well as enzymes such as DNA ligase and DNA polymerase.

In other embodiments, a dual binders (DB) assay is employed, which utilizes a bi-specific detection agent consisting of two Fab fragments with fast off-rate kinetics joined by a flexible linker (Van dieck et al., 2014 *Chemistry & Biology* Vol. 21(3):357-368). In principle, because the dual binders comprise Fab fragments with fast off-rate kinetics, the dual binders are washed off if only one of the Fab fragments is bound to its epitope (simultaneous cooperative binding of both Fab fragments of the dual binder prevents dissociation of the dual binder and leads to positive staining/visibility).

According to another approach disclosed in International Publication WO2014/139980, which is encompassed in the practice of the present disclosure, proximity assays and tools are described, which employ a biotin ligase substrate and an enzyme to perform a proximity assay. The method provides detection of target molecules and proximity while maintaining the cellular context of the sample. The use of biotin ligase such as an enzyme from *E. coli* and peptide substrate such as amino-acid substrate for that enzyme provides for a sensitive and specific detection of protein-protein interactions in FFPE samples. Because biotin ligase can efficiently biotinylate appropriate peptide substrate in the presence of biotin and the reaction can only occur when the enzyme makes physical contact with the peptide substrate, biotin ligase and the substrate can be separately conjugated to two antibodies that recognize targets of interest respectively.

In some embodiments, the level/amount of one or more biomarker proteins and/or their cellular location/distribution may be compared to a reference which may include a sample from a subject not receiving a therapy (e.g., an anti-infective therapy, cytotoxic therapy and/or immunotherapy). In some embodiments, a reference may include a sample from the same subject before receiving a therapy (e.g., an anti-infective therapy, cytotoxic therapy and/or immunotherapy). In some embodiments, a reference may include a reference value from one or more samples of other subjects receiving a therapy (e.g., an anti-infective therapy, cytotoxic therapy and/or immunotherapy). For example, a population of patients may be treated, and a mean, average, or median value for level/amount of the at least one RTT biomarker and/or their cellular location/distribution may be generated from the population as a whole. A set of samples obtained from diseases having a shared characteristic (e.g., the same cancer type or pathogenic infection and/or stage, or exposure to a common therapy) may be studied from a population, such as with a clinical outcome study. This set may be used to derive a reference, e.g., a reference number, to which a patient's sample may be compared.

Certain aspects of the present disclosure relate to measurement of the level/amount of one or more RTT biomarkers in a sample. In some embodiments, a sample may include cancer cells. In some embodiments, the sample may be a peripheral blood sample (e.g., from a patient having a tumor or pathogenic infection). In some embodiments, the sample is a tumor sample. A tumor sample may include cancer cells, lymphocytes, leukocytes, stroma, blood vessels, connective tissue, basal lamina, and any other cell type in association with the tumor. In some embodiments, the sample is a tumor tissue sample containing tumor-infiltrating leukocytes. In some embodiments, the sample may be processed to separate or isolate one or more cell types (e.g., leukocytes). In some embodiments, the sample may be used without separating or isolating cell types.

A tumor sample may be obtained from a subject by any method known in the art, including without limitation a biopsy, endoscopy, or surgical procedure. In some embodiments, a tumor sample may be prepared by methods such as freezing, fixation (e.g., by using formalin or a similar fixative), and/or embedding in paraffin wax. In some embodiments, a tumor sample may be sectioned. In some embodiments, a fresh tumor sample (i.e., one that has not been prepared by the methods described above) may be used. In some embodiments, a tumor sample may be prepared by incubation in a solution to preserve mRNA and/or protein integrity.

In some embodiments, the sample may be a peripheral blood sample. A peripheral blood sample may include white blood cells, PBMCs, and the like. Any technique known in the art for isolating leukocytes from a peripheral blood sample may be used. For example, a blood sample may be drawn, red blood cells may be lysed, and a white blood cell pellet may be isolated and used for the sample. In another example, density gradient separation may be used to separate leukocytes (e.g., PBMCs) from red blood cells. In some embodiments, a fresh peripheral blood sample (i.e., one that has not been prepared by the methods described above) may be used. In some embodiments, a peripheral blood sample may be prepared by incubation in a solution to preserve mRNA and/or protein integrity.

In some embodiments, responsiveness to therapy may refer to any one or more of: extending survival (including overall survival and progression free survival); resulting in an objective response (including a complete response or a partial response); or improving signs or symptoms of cancer. In some embodiments, responsiveness may refer to improvement of one or more factors according to the published set of RECIST guidelines for determining the status of a tumor in a cancer patient, i.e., responding, stabilizing, or progressing. For a more detailed discussion of these guidelines, see, Eisenhauer et al. (2009 *Eur J Cancer* 45: 228-47), Topalian et al. (2012 *N Engl J Med* 366:2443-54), Wolchok et al. (2009 *Clin Can Res* 15:7412-20) and Therasse et al. (2000 *J. Natl. Cancer Inst.* 92:205-16). A responsive subject may refer to a subject whose cancer(s) show improvement, e.g., according to one or more factors based on RECIST criteria. A non-responsive subject may refer to a subject whose cancer(s) do not show improvement, e.g., according to one or more factors based on RECIST criteria.

In some embodiments, conventional response criteria may not be adequate to characterize the activity of an anti-cancer therapy, which can produce delayed responses that may be preceded by initial apparent radiological progression, including the appearance of new lesions. Therefore, modified response criteria have been developed that account for the possible appearance of new lesions and allow radiological progression to be confirmed at a subsequent assessment. Accordingly, in some embodiments, responsiveness may refer to improvement of one of more factors according to immune-related response criteria (irRC). See, e.g., Wolchok et al. (2009, supra). In some embodiments, new lesions are added into the defined tumor burden and followed, e.g., for radiological progression at a subsequent assessment. In some embodiments, presence of non-target lesions is included in assessment of complete response and not included in assessment of radiological progression. In some embodiments, radiological progression may be determined only on the basis of measurable disease and/or may be confirmed by a consecutive assessment ≥4 weeks from the date first documented.

In some embodiments, responsiveness may include immune activation. In some embodiments, responsiveness may include treatment efficacy. In some embodiments, responsiveness may include immune activation and treatment efficacy.

3. Biomarker Panels

The biomarkers of the present disclosure can be used in predictive and/or prognostic tests to assess, determine, and/or qualify (used interchangeably herein) response to therapy signature status in a patient and therefore, direct treatment of the patient. The phrase "response to therapy signature status" includes a high response to therapy signature (RT high) and a low response to therapy signature (RT low). Based on this status, further procedures may be indicated, including additional tests or therapeutic procedures or regimens.

These and other biomarkers are disclosed herein, and it is understood that when combinations, subsets, interactions, groups, etc., of these biomarkers are disclosed that while specific reference of each various individual and collective combinations and permutation of these compounds may not be explicitly disclosed, each is specifically contemplated and described herein. Thus, if a panel of biomarkers A, B, and C are disclosed as well as a class of biomarkers D, E, and F and an example of a combination panel A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of using the disclosed biomarkers. Thus, if there are a variety of additional steps that can be performed, it is understood that each of these additional steps can be performed with any specific embodiment or combination of embodiments of the disclosed methods.

The response to therapy signature panel suitably includes PD-L2 (e.g., one or both of nuclear PD-L2 and extranuclear PD-L2) and at least one nuclear binding partner of PD-L2, (e.g., a histone polypeptide such as but not limited to an H2A polypeptide, an H2AX polypeptide and an H4 polypeptide). Non-limiting examples of these signature include: nuclear PD-L2:extranuclear PD-L2; PD-L2:H2A; PD-L2:H2AX; and PD-L2:H4.

The power of an assay to correctly predict response to therapy is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker signatures of the present disclosure may show a statistical difference in different response to therapy statuses of at least $p<0.05$, $p<10^{-2}$, $p<10^{-3}$, $p<10^{-4}$ or $p<10^{-5}$. Predictive or prognostic tests that use these biomarkers may show an ROC of at least 0.6, at least about 0.7, at least about 0.8, or at least about 0.9.

In certain embodiments, the biomarkers are measured in a patient sample using the methods described herein and a response to therapy signature status is calculated. In particular embodiments, the measurement(s) may then be compared with a relevant predictive or prognostic amount(s), cut-off(s), or multivariate model scores that distinguish a high therapy response signature (RT high) status from a low therapy response signature (RT low) status. The predictive or prognostic amount(s) represents a measured amount of a biomarker(s) above which or below which a patient is classified as having a particular therapy response signature status. As is well understood in the art, by adjusting the particular predictive or prognostic cut-off(s) used in an assay, one can increase sensitivity or specificity of the assay depending on the preference of the skilled person. In particular embodiments, the particular predictive or prognostic cut-off can be determined, for example, by measuring the level or amount of biomarkers in a statistically significant number of samples from patients with different response to therapy signature statuses, and drawing the cut-off to suit the desired levels of specificity and sensitivity.

Furthermore, in certain embodiments, the values measured for biomarkers of a biomarker panel are mathematically combined and the combined value is correlated to the underlying predictive or prognostic question of high or low response to therapy signature. Biomarker values may be combined by any appropriate mathematical method known in the art. Well-known mathematical methods for correlating a biomarker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present disclosure. In one embodiment, the method used in a correlating a biomarker combination of the present disclosure is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

The biomarkers of the present disclosure can also be used in predictive and/or prognostic tests to assess, determine, and/or qualify disease (e.g., severity and/or progression) and/or immune signature status in a patient. In these embodiments, a patient's RT signature status is inversely correlated to the patient's disease signature status. For example, an RT high correlates with a low disease (e.g., severity and/or progression) signature status in the patient and an RT low correlates with a high disease (e.g., severity and/or progression) signature status in the patient. Conversely, a patient's RT signature status directly correlates with the patient's immune signature status. For example, an RT high correlates with a high immune signature status in the patient and an RT low correlates with a low immune signature status in the patient.

4. Generation of Classification Algorithms for Qualifying Response to Therapy Signature Status In some embodiments, data that are generated using samples such as "known samples" can then be used to "train" a classification model. A "known sample" is a sample that has been pre-classified. The data that are used to form the classification model can be referred to as a "training data set". The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition.

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al., "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the disclosure can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

In some embodiments any of the classification methods disclosed herein may be performed at least in part by one or more computers and/or may be stored in a database on a non-transitory computer medium. In some embodiments any of the classification methods disclosed herein may be embodied or stored at least in part on a computer-readable medium having computer-executable instructions thereon. In some embodiments a computer-readable medium comprises any non-transitory and/or tangible computer-readable medium.

5. Kits

The present disclosure also extends to kits for determining level/amounts and/or cellular localization of RTT biomarkers disclosed herein, which include reagents that allow detection and/or quantification of the biomarkers. Such reagents include, for example, compounds or materials, or sets of compounds or materials, which allow quantification of the biomarkers. In specific embodiments, the compounds, materials or sets of compounds or materials permit determining the level of a biomarkers, including without limitation the extraction of RNA material, the determination of the level of a corresponding RNA, etc., primers for the synthesis of a corresponding cDNA, primers for amplification of DNA, and/or probes capable of specifically hybridizing with the RNAs (or the corresponding cDNAs) encoded by the genes, TaqMan probes, proximity assay probes, ligases, antibodies etc.

The kits may also optionally include appropriate reagents for detection of labels, positive and negative controls, washing solutions, blotting membranes, microtiter plates, dilution buffers and the like. For example, a protein-based detection kit may include (i) at least one PD-L2 polypeptide (which may be used as a positive control), (ii) one or more antigen-binding molecules that bind specifically to a PD-L2 polypeptide, and/or (iii) at least one nuclear binding partner of PD-L2 including histone polypeptides such as but not limited to an H2A polypeptide, an H2AX polypeptide and an H4 polypeptide, or fragments thereof. The antigen-binding molecules are suitably detectably labeled. The kit can also feature various devices (e.g., one or more) and reagents (e.g., one or more) for performing one of the assays described herein; and/or printed instructional material for using the kit to quantify the level/amount of an RTT biomarker. The reagents described herein, which may be optionally associated with detectable labels, can be presented in the format of a microfluidics card, a chip or chamber, a microarray or a kit adapted for use with the assays described herein.

Materials suitable for packing the components of the diagnostic kits may include crystal, plastic (polyethylene, polypropylene, polycarbonate and the like), bottles, vials, paper, envelopes and the like. Additionally, the kits of the disclosure can contain instructional material for the simultaneous, sequential or separate use of the different components contained in the kit. The instructional material can be in the form of printed material or in the form of an electronic support capable of storing instructions such that they can be read by a subject, such as electronic storage media (magnetic disks, tapes and the like), optical media (CD-ROM, DVD) and the like. Alternatively or in addition, the media can contain Internet addresses that provide the instructional material.

6. Patient Classification and Treatment Management

The present disclosure extends to methods of selecting or identifying individuals who are appropriate candidates for treatment with a therapy (e.g., an anti-infective therapy, cytotoxic therapy, immunotherapy, etc.) for treatment of a disease (e.g., a disease caused by a pathogenic infection or cancer). Such individuals include patients that are predicted to be responsive to the therapy and thus have an increased likelihood of benefiting from administration of the therapy relative to other patients having different characteristic(s) (e.g., non-responsiveness to the therapy). In certain embodiments an appropriate candidate is one who is reasonably likely to benefit from treatment or at least sufficiently likely to benefit as to justify administering the treatment in view of its risks and side effects. The disclosure also encompasses methods of selecting or identifying individuals who are not appropriate candidates for treatment with a therapy (e.g., an anti-infective therapy, cytotoxic therapy and/or immunotherapy, etc.) for treatment of a disease (e.g., a disease caused by a pathogenic infection or cancer). Such individuals include patients that are predicted to be non-responsive or weakly responsive to the therapy and thus have a decreased likelihood of benefiting from administration of the therapy relative to other patients having different characteristic(s) (e.g., responsiveness to the therapy), or a low or substantially no likelihood of benefiting from such treatment, such that it may be desirable to use a different or additional treatment. In some embodiments, whether a subject is an appropriate candidate for therapy with a therapy is determined based on an assay of at least one RTT biomarker in a sample obtained from a patient, as described herein.

In some aspects described herein are methods of determining, for example based on an assay of at least one RTT biomarker, the likelihood that a patient in need of treatment of a disease (e.g., a disease caused by a pathogenic infection or cancer) will respond to treatment with a therapy (e.g., an anti-infective therapy, cytotoxic therapy and/or immunotherapy, etc.) and/or of identifying and/or selecting a patient to receive such treatment. In specific embodiments, the therapy is an immunotherapy, suitably with an anti-immune checkpoint inhibitor. The phrase "treatment with an immune checkpoint inhibitor", also referred to as "immune checkpoint inhibitor treatment", "therapy with an immune checkpoint inhibitor", or "immune checkpoint inhibitor therapy", encompasses embodiments pertaining to treatment with a single immune checkpoint inhibitor and embodiments pertaining to treatment with two or more immune checkpoint inhibitors in combination. In some embodiments immune checkpoint inhibitor treatment comprises inhibiting two or more different immune checkpoint pathways using a single agent or using two or more separate agents.

In order that the disclosure may be readily understood and put into practical effect, particular preferred embodiments will now be described by way of the following non-limiting examples.

EXAMPLES

Example 1

Nuclear Translocation of PD-L2 Expression on Human DCs Correlates with Malaria Severity To show that PD-L1 and PD-L2 expressed on DCs influenced malarial immunity, eleven malaria-naïve, healthy human volunteers were infected with either 1800 or 2700 $P.$ $falciparum$ infected red cells (pRBC) in 3 clinical trials for drug development and their blood examined before and ~8 days after challenge. In all eleven volunteers, ~82% of DCs expressed PD-L1 before infection, and there were significant reductions (~18%) to the percentage of DCs expressing this ligand by day 8 of infection (FIG. 1A). In contrast, while ~78% of DCs also expressed PD-L2 before infection, 8 of 11 individuals showed a 23-37% reduction in percentages of PD-L2+ DCs after infection (FIG. 1B). Notably, there was a significant inverse correlation between parasitemia and percentage PD-L2-expressing DCs post-infection (p.i.) (FIG. 1C). In effect, higher PD-L2 expression was associated with better control of the infection.

To determine if PD-L2 translocation to the nucleus of DC, contributed to these observed changes in surface PD-L1 and PD-L2 expression, DCs were isolated from the blood of 5 volunteers at day 0 and day 8 for microscopy (FIG. 1D). At day 0, PD-L1 was evenly distributed over the cell surface while PD-L2 appeared speckled (FIG. 1D). After 8 days, 3 of 5 volunteers (RO3, RO4 and RO6) who showed the highest loss in surface PD-L1 and PD-L2 expression by flow cytometry, now had PD-L2 expression in the nucleus. In contrast, volunteers R07 and RO8 who showed lesser changes to PD-L1 and PD-L2 by flow cytometry had an abundance of surface PD-L1 and PD-L2 by microscopy and only very occasionally was a small amount of PD-L2 found in the nucleus. Overall, PD-L2 was found to translocate to the nucleus of DCs during malaria and the level of translocation directly correlated with the severity of the infection.

Example 2

Nuclear Translocation of PD-L2 Expression on Mouse DCs Correlates with Mortality To understand the biological relevance of nuclear PD-L2, mouse models of lethal ($P.$ $yoelii$ YM) malaria described previously[7,9] were investigated. DCs were isolated from spleens of mice infected with $P.$ $yoelii$ YM, permeabilized and labeled for confocal microscopy to locate PD-L2 and PD-L1 (FIG. 2A) and used MHC Class II-labeling (FIG. 2B) to define the cell surface. During lethal infections, >70% of DCs expressed nuclear PD-L2 which did not co-localize with PD-L1 (FIG. 2A) or MHC Class II (FIG. 2B).

Figure 2:
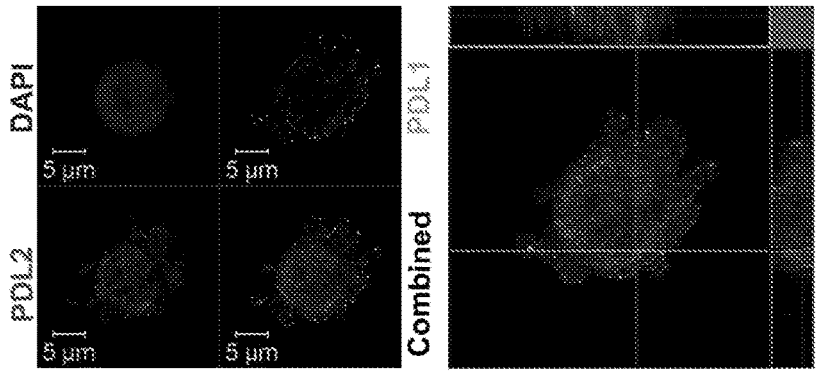
FIG. 2 is a photographic and graphical representation showing that nuclear PD-L2 in DCs from malaria-infected mice is associated with poor immune responses and lethality. C57BL/6 mice (WT) and PD-L2 knockout mice (on a C57BL/6 background; Pdcdlg2$^{-/-}$) were infected with *P. yoelii* YM and DCs isolated on day 7. (A, B) Representative microscopy showing DCs from WT mice expressing (A) PD-L1 and PD-L2 and (B) MHC class II and PD-L2 after infection. The orthogonal View with blue, red and green lines highlights a point in 3D z-stack where red PD-L2 co-localizes with blue of DAPI in nuclei. (C, D) DCs from naïve and *P. yoelii* YM infected mice were fractionated into (C) surface/cytoplasmic and (D) Nuclear fractions, run on SDS page and Western blots labelled for PD-L2 and corresponding control proteins. (E, F) WT and Pdcdlg2$^{-/-}$ mice were infected with *P. yoelii* YM and monitored for (E) Survival and (F) Mean percent parasitemia for a typical course of infection, for 40 days, in 2 replicate experiment with (total N=9).
Figure 2:
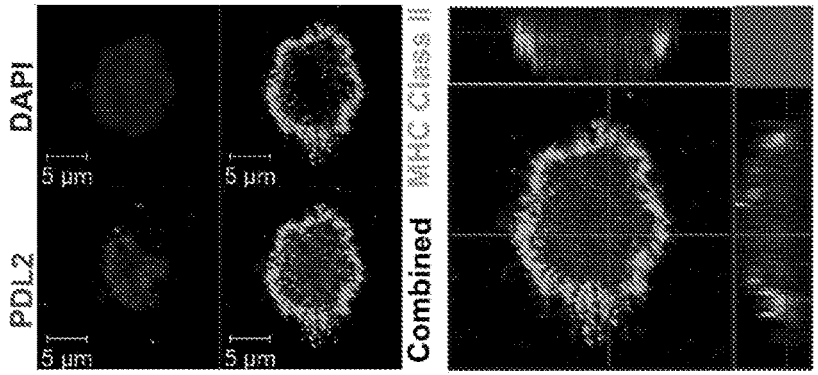
Figure 2:
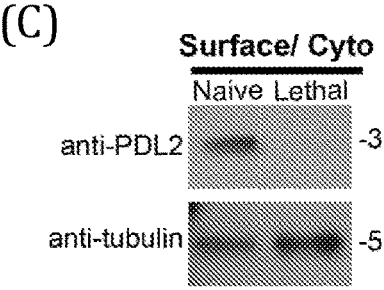
Figure 2:
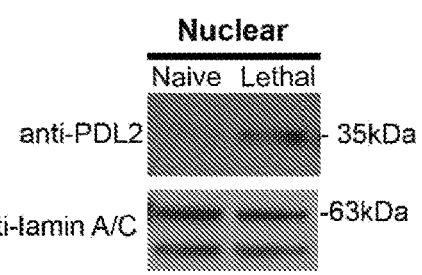
Figure 2:
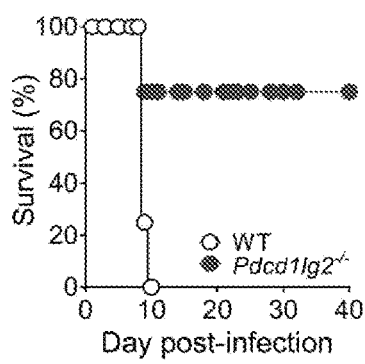
Figure 2:
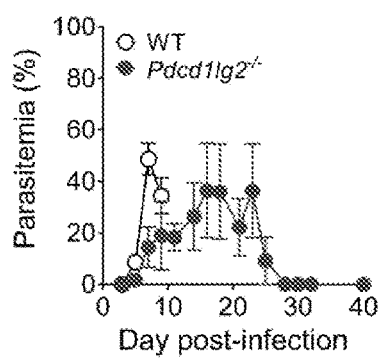

To confirm and quantify nuclear and surface localization of PD-L2 during malaria, DCs from naïve mice and mice infected with lethal malaria were fractionated into cell membrane\ cytoplasmic or nuclear proteins, and western blots of these proteins labelled for PD-L2 (FIGS. 2C and D). These blots revealed DCs from naïve mice had surface PD-L2 (FIG. 2C). In contrast, PD-L2 was found in the nucleus of DCs from lethal malaria compared to negligible levels in DCs from naïve mice (FIG. 2D).

Finally, given that the present inventor has previously established that DCs mediate survival of lethal $P.$ $yoelii$ malarial infections[7,10,11] and that DCs from these lethal infections had predominantly nuclear PD-L2 (FIGS. 2A, B and D), Pdcd1lg2$^{-/-}$ mice (PD-L2 deletion on a C57BL/6J background)[12] and C57BL/6J WT mice were infected with lethal $P.$ $yoelii$ YM. All WT mice succumbed to the infection in 10 days, while 75% of mice with no PD-L2 survived (FIG. 2E) and cleared the infection (FIG. 2F). Overall, these studies indicated that PD-L2, which is localized in the nucleus of DCs, was causing lethality of mice.

Example 3

PD-L1 and PD-L2 Levels Decrease on DCs in Patients with Advanced Melanoma

Figure 3:
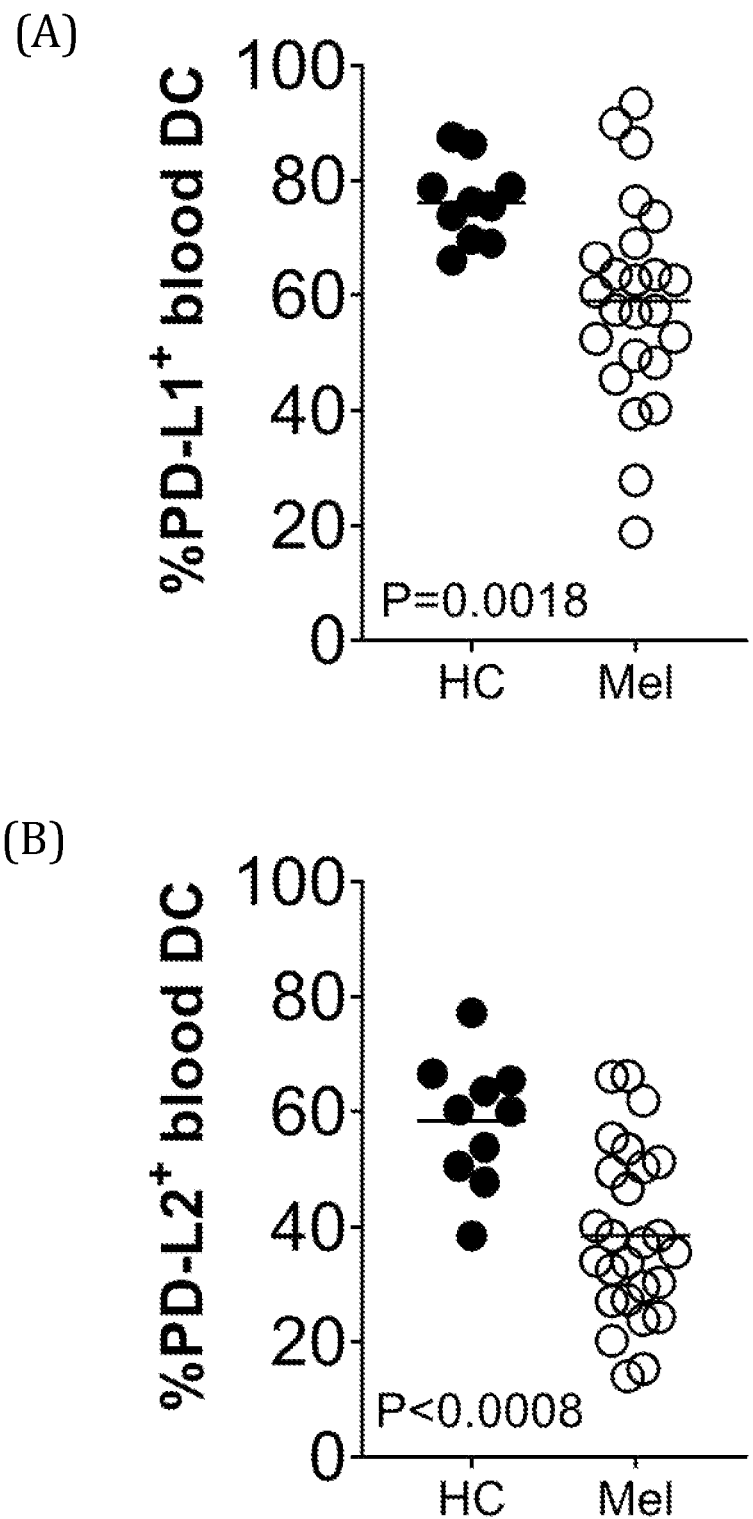
FIG. 3 is a graphical representation showing PD-L1 and PD-L2 expression on DCs from healthy controls (HC) and patients with Stage IV melanoma (Mel). PBMC were taken from eleven Red Cross blood donors and twenty three patients with stage IV melanoma and blood examined for percentage of Lineage-MHC Class II$^+$ CD11c$^+$ DC expressing (A) PD-L1 and (B) PD-L2. Significance between samples was analyzed by using the non-parametric Mann-Whitney U test based on 2-sided tail.

To determine if the changes to DCs during malaria, were relevant to cancer, the present inventor examined DCs from Stage IV melanoma patients compared to blood from Red Cross donors. While ~80% of lineage negative, MHC Class II+CD11c+ DCs express PD-L1 (FIG. 3A) and PD-L2 (FIG. 3B), the proportion of DCs expressing PD-L1 and PD-L2 are significantly reduced in melanoma patients. The present inventor next examined if this loss correlated to exhausted T-cells. For this, CD3+ CD8+ T-cells were examined for high expression of PD-1 and Tim3 which are an indication of exhausted T-cells[13] which fail to respond to PD-1 therapy[14]. While there was no correlation between PD-L1 expression on DCs and CD3+ CD8+ T-cells with high PD-1 expression (FIG. 4A), there was a significant inverse correlation between PD-L2 expression on DCs with PD-1 (FIG. 4B) and TIM3 on CD3⁺CD8⁺ T-cells (FIG. 4C). These studies showed that loss of PD-L2 expression was associated with exhausted CD8⁺ T-cells, unlikely to respond to PD-1 blockade therapy[14].

Example 4

Loss of Surface PD-L2 on DCs Correlates with Increased Nuclear PD-L2

Figure 4:
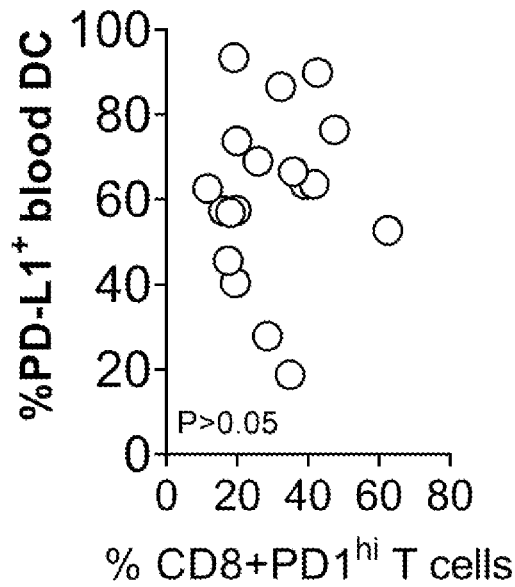
FIG. 4 is a graphical representation showing that loss of surface PD-L2 on blood DCs correlates with T-cell exhaustion. PBMC were taken from eighteen patients with stage IV melanoma and blood examined for percentage of MHC Class II$^+$ CD11c$^+$ DC expressing (A) PD-L1 and (B) PD-L2 and their association with CD8$^+$ T-cells expressing high PD-1 levels. (C) PD-L2 and their association with CD8$^+$ T-cells expressing high TIM3 levels. The P value is testing the null hypothesis that the overall slope is zero. $R^2$ is a measure of the goodness of the fit.
Figure 4:
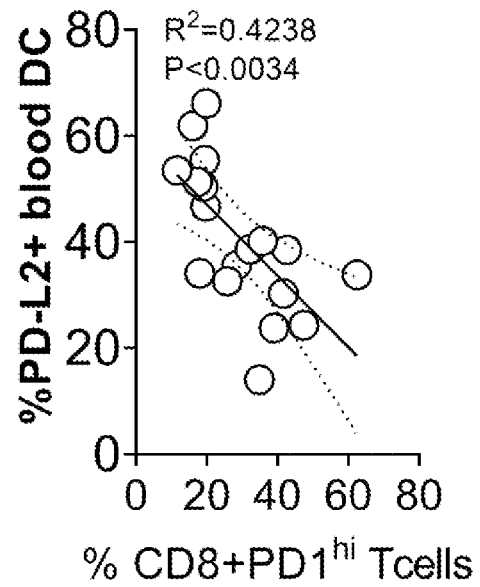
Figure 4:
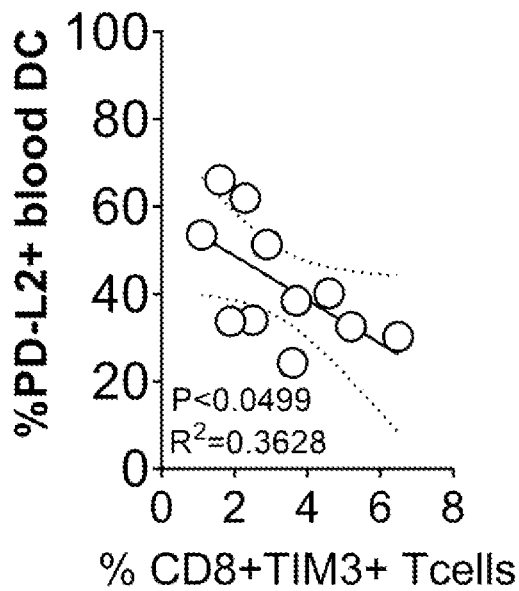
Figure 5:
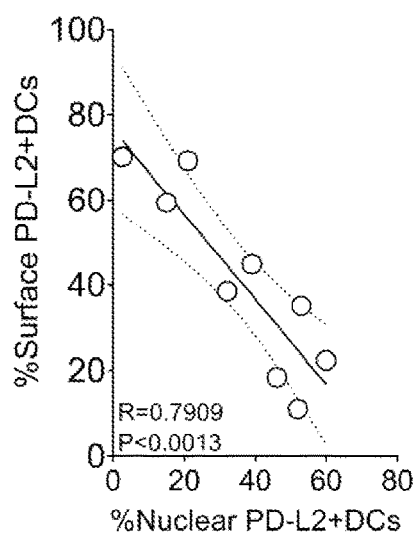
FIG. 5 is a graphical representation showing that loss of surface PD-L2 on DCs correlates with increased nuclear PD-L2. (A) Microscopy was used to measure the correlation between surface and nuclear PD-L2 in 9 patients with stage IV melanoma. The P value is testing the null hypothesis that the overall slope is zero. $R^2$ is a measure of the goodness of the fit. (B) Three representative examples of microscopy showing the distribution of PD-L2 on the surface and within the nucleus of blood DCs from patients with decreasing surface PD-L2 expression.
Figure 5:
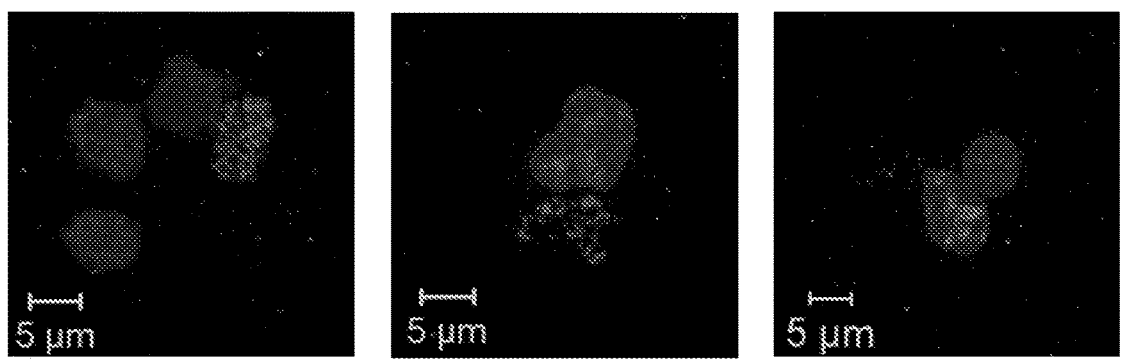

To determine if PD-L2 also translocates to the nucleus of DCs in melanoma patients, DCs were isolated form the blood of 9 melanoma patients, identified in FIG. 4 to have a range of PD-L2 expression. Microscopy was used to identify the percentage of DCs with nuclear PD-L2 and correlate this with surface expression (FIG. 5A). There was an inverse correlation, in that when a high percentage of DCs expressed surface PD-L2 (60-70%), the proportion of DCs with nuclear PD-L2 was low (2-21%). Conversely, DCs with low percentage of surface PD-L2 (11-22%), had high proportion of DCs with nuclear PD-L2 (46-60%). FIG. 5B provides microscopy of representative examples of DCs with differing surface and nuclear PD-L2. Of note, samples with moderate surface PD-L2, also had nuclear PD-L2.

Example 5

Loss of Surface PD-L2 on Tumor Cells Correlates with Increased Nuclear PD-L2

Figure 6:
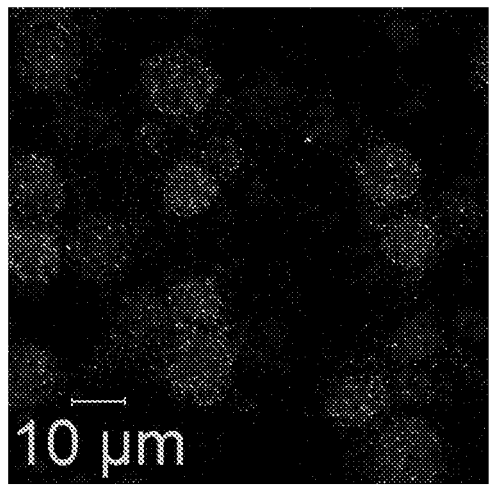
FIG. 6 is a photographic representation showing nuclear PD-L2 accumulation in CT26 tumour cells. BALB/c mice were implanted with CT26 colon tumor cells and tumors were harvested for microscopy at day 15 when tumors had reached ~100-200 mm$^3$ and again at day 21 when tumours reached ~500 mm$^3$. Harvested tumors were labeled for CD45-magnetic beads and placed on magnet to remove hematopoietic cells. Tumour cells were placed on slides and labeled for DAPI (blue), PD-L1 (green), and PD-L2 (red). Co-localization between PD-L2 and the nucleus appears pink.
Figure 6:
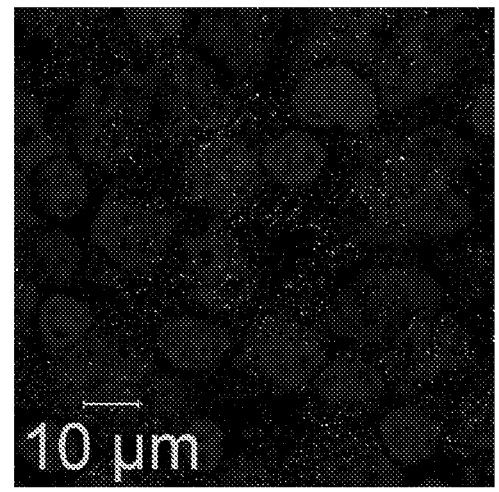
Figure 6:
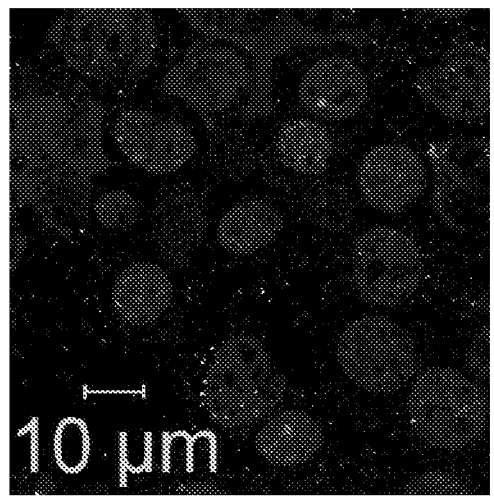
Figure 6:
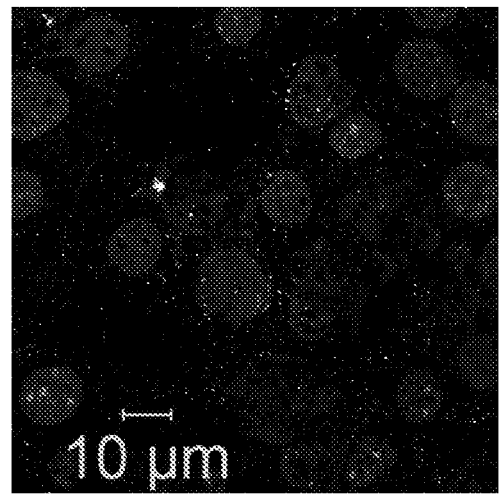

To determine if PD-L2 translocated to the nucleus of tumor cells, mice were implanted with CT26 tumors and tumors were harvested for microscopy at day 15 when tumors had reached ~100-200 mm³ and again at day 21 when tumors reached ~500 mm³. The microscopy revealed the presence of nuclear PD-L2 in ~30-50% of tumor cells along with surface expression at day 15 (FIG. 6A) and this increased to 75% of tumor cells with nuclear PD-L2 but minimal amounts on the surface by day 21 (FIG. 6B). Significantly, these data show that increased nuclear PD-L2 correlates with disease progression.

Preliminary experiments by the present inventor have also suggested that PD-L2 translocates to the nucleus of immune effector cells, including B-cells and T-cells in patients with advanced disease.

Discussion of Examples 1-5

PD-1 therapy only has overall long term clinical benefit for ~30% of cancer patients. Selecting patients based on PD-L1 expression on tumor cells, like melanoma patients, has marginally improved the success rate to 38-50%. A correlation exists between PD-L1 expression on tumors and the efficacy of anti-PD-1 therapy in melanoma, non-small cell lung cancer and renal cell carcinoma[16]. However, clinical trials also showed that some patients display a clinical response regardless of tumor PD-L1 expression levels, while others do not benefit from treatment despite the expression of PD-L1 on tumor cells. Taken together, these findings strongly support the hypothesis that other factors are relevant for the efficacy of immunotherapies[17].

Many biomarker investigations have therefore focused on examining clinical laboratory parameters to determine if any correlate with outcomes in patients receiving checkpoint inhibition therapy[18]. However, most studies focus on T-cells or cancer gene signatures[1,2,6,19,20] and the role of PD-L2 in immunity has been generally overlooked. This suggests that PD-L1 expression is not the most significant marker and factors other than PD-1-mediated exhaustion are in place.

The present inventor proposes that selection of patients for treatment with a therapy, including an immunotherapy should consider any one or more of the following factors:

(1) Antigen-presenting cells such as DCs modulate adaptive immune responses essential for controlling pathogenic infections and tumors. The results presented herein show that DCs with nuclear PD-L2 are highly immunocompromised and/or immunosuppressive and thus patients with abundant nuclear PD-L2 in DCs are unlikely to benefit from therapy, including PD-1/PD-L1 blockade or similar therapies as their DCs are immunocompromised and/or immunosuppressive. In contrast, patients with low level of nuclear PD-L2 but high surface levels of PD-L2 have immunocompetent DCs. Accordingly, patients could be chosen based on the status of nuclear PD-L2 in antigen-presenting cells as a surrogate marker of the health of their immune system.

(2) Immune effector cells such as B-cell and T-cells also modulate adaptive immune responses essential for controlling pathogenic infections and tumors. Preliminary data suggest that like DCs, B-cell and T-cells with nuclear PD-L2 are highly immunocompromised and/or immunosuppressive and thus patients with abundant nuclear PD-L2 in B-cells and T-cells are unlikely to benefit from therapy, including PD-1/PD-L1 blockade or similar therapies as their immune effector cells are immunocompromised and/or immunosuppressive. In contrast, patients with low level of nuclear PD-L2 but high surface levels of PD-L2 have immunocompetent immune effector cells. Accordingly, patients could be chosen based on the status of nuclear PD-L2 in immune effector cells as a surrogate marker of the health of their immune system.

(3) A factor for selecting cancer patients for treatment with a therapy is the PD-L2 nuclear localization status of patient tumors. According to results presented herein, tumors with predominantly nuclear localized PD-L2 have progressed substantially and are less likely to respond to a therapy, including an immunotherapy. Thus patients with less or no nuclear PD-L2 in their tumor cells are likely to benefit the most by treatment with the therapy.

Example 6

Figure 7:
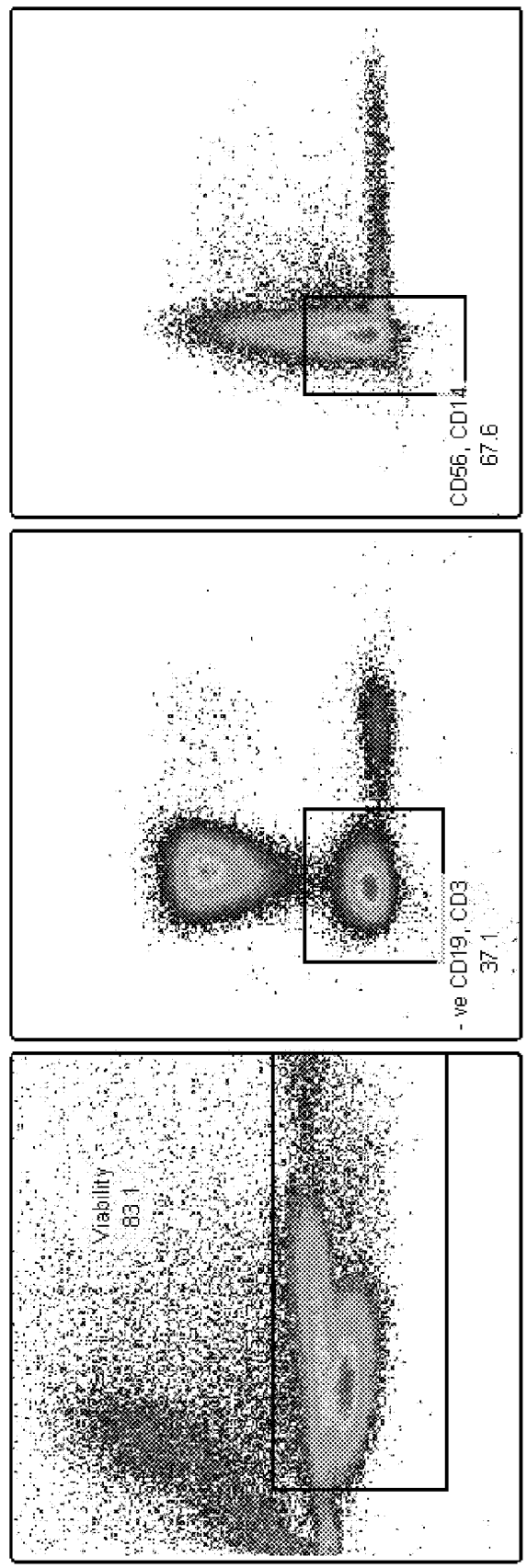
FIG. 7 is a graphical representation showing the gating strategy and detection of nuclear PD-L2 bound to Histone H2A by proximity ligase assay (PLA). PBMCs from three patients with advanced melanomas were labelled for PD-L2 and histone H2A in the nucleus using a PLA. (A) Gating strategy used in flow cytometry to study viable cells which did not express CD19, CD3, CD56 or CD14. (B) CD11c cells which did not express CD19, CD3, CD56 or CD14 labelled to detect PD-L2 and histone H2A being within 40 nM proximity. (C) CD11c cells which did not express CD19, CD3, CD56 or CD14 labelled with control antibodies and PLA.
Figure 7:
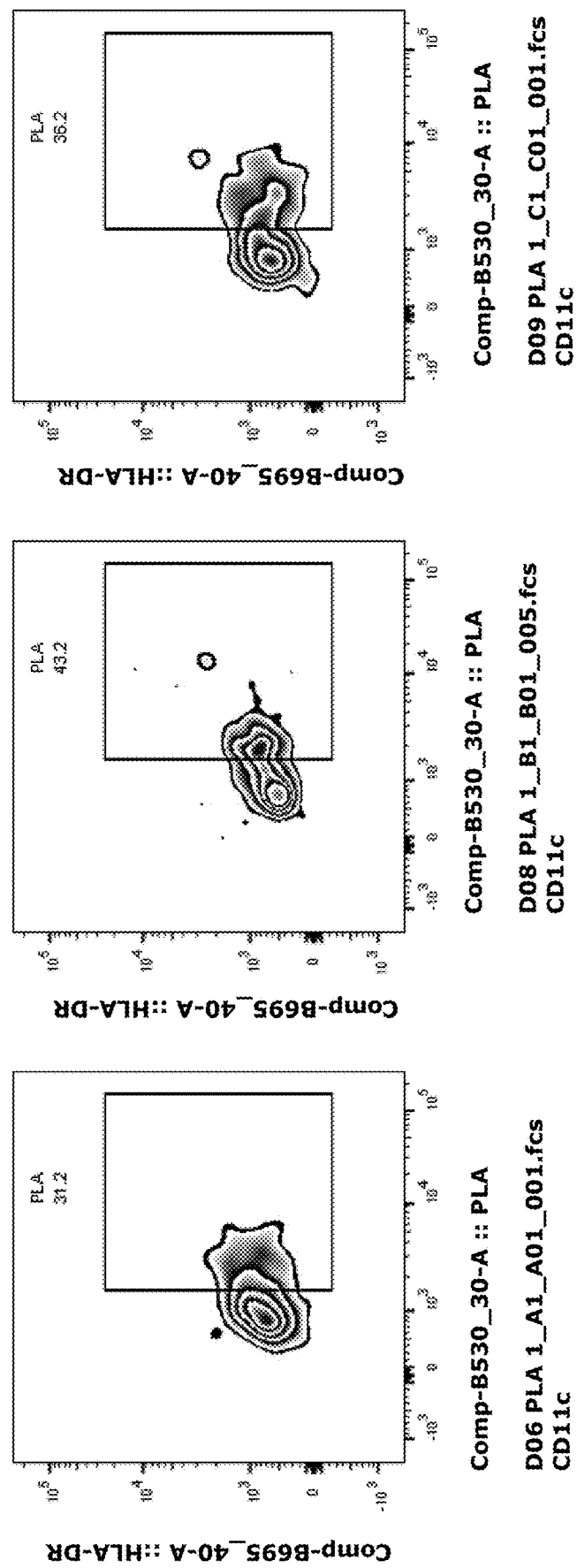
Figure 7:
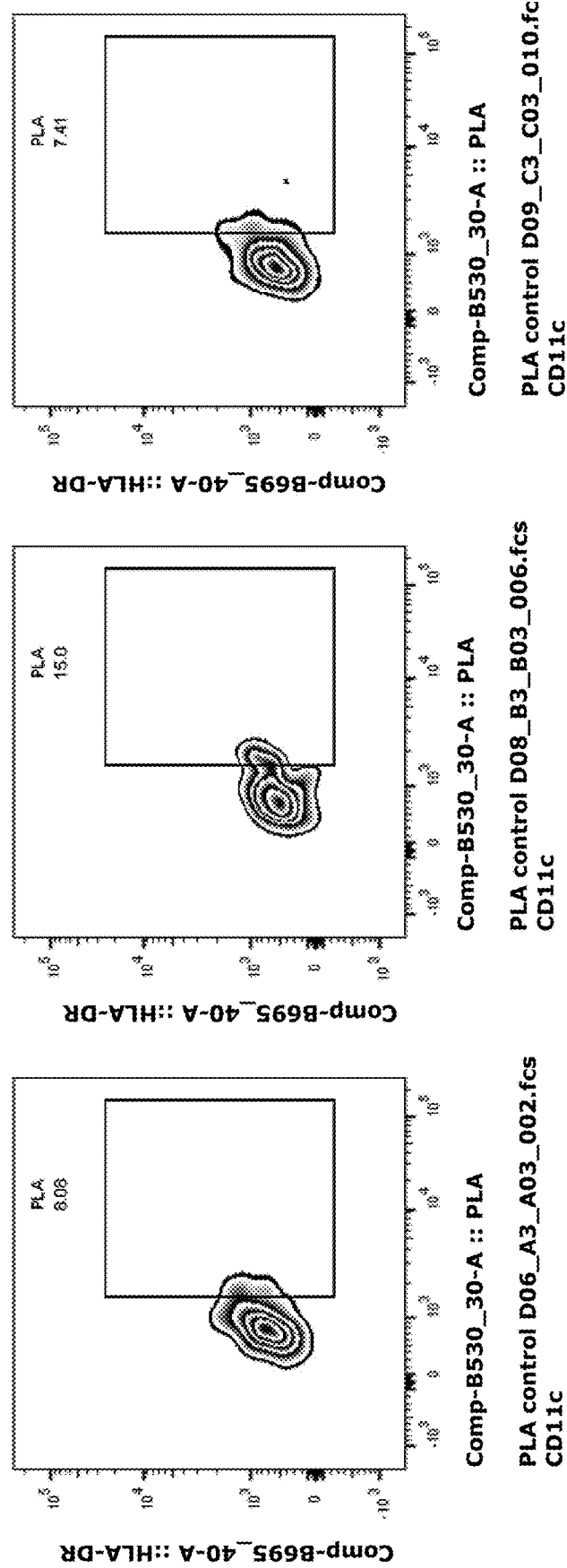
Figure 8:
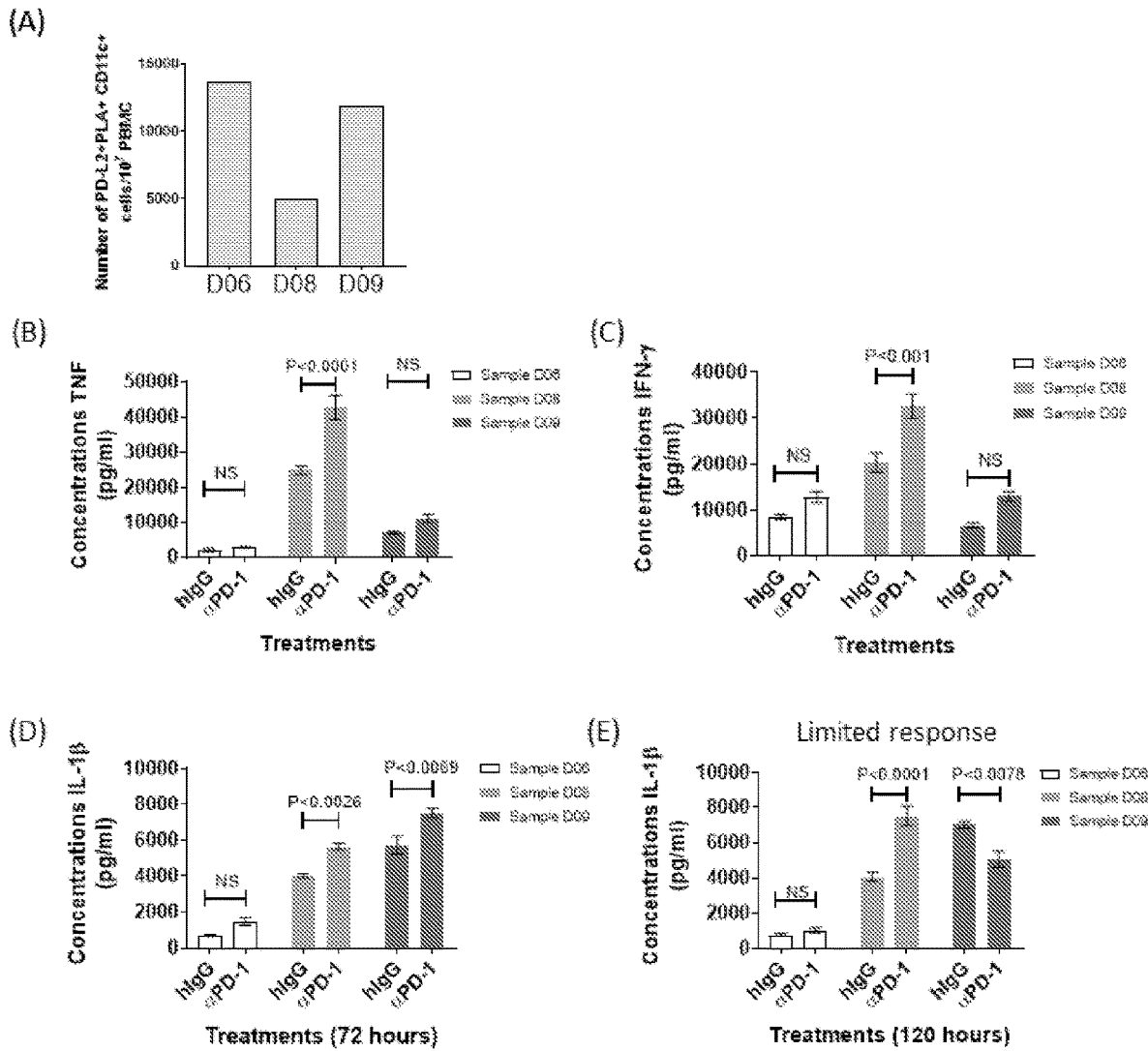
FIG. 8 is a graphical representation showing the association between number of DCs with nuclear PD-L2 measured by PLA in PBMCs from melanoma patients and cytokines released by PBMC when stimulated. Proximity ligase assay was applied to PBMCs from 3 melanoma patients to measure PD-L2 which was in close proximity to histone H2A to confirm nuclear localization. (A) Number of Lineage negative (CD3−CD19−CD56−CD14−)CD11c+ DCs which were PLA+ (PD-L2+H2A+) in 10 million PBMCs. (B-E) PBMCs were cultured with anti-CD3 antibody and treated with anti-PD1 antibody (Nivolumab) or control IgG. Supernatants were collected after 72 and/or 120 hours and tested for cytokines (B) TNF; (C) IFN-γ; or (D-E) IL-1β. Error bars represent SEM. Significance for assays was analyzed using the non-parametric Mann-Whitney U test based on two-sided tail (NS indicates no significance).

Increase of Nuclear PD-L2 Results in Reduced Response to Anti-Cancer Immunotherapy The above data show a correlation between nuclear PD-L2 in DCs and exhausted PD1$^{hi}$ T-cell phenotype (see, FIG. 4B) during cancer (melanoma) where these cells are unable to respond with cytokine secretion and poor control of parasitemia during malaria (FIG. 1). Furthermore, PD-1 blockade therapy is given to melanoma patients to prevent T-cell exhaustion but only ~50% respond and the response is short-lived in many patients. To determine if nuclear PD-L2 in DCs prevents the success of PD-1 therapy, and thus prognostic of patients who would not respond, we compared responses in three melanoma patients. Thus, DCs in PBMCs obtained from the patients were tested using a PLA assay to determine the number of cells which had PD-L2 within 40 nm of Histone H2A, thus confirming the PD-L2 protein was in the nucleus. The rationale for this experiment being that PD-L2 in the cytoplasm could not bind histones in the nucleus as they are separated by the nuclear membrane. FIGS. 7 (A and B) show data from the PLA assay. FIG. 8A shows the numbers of DCs with nuclear PD-L2 in $10^7$ PBMCs for the three melanoma patients.

PMBCs from the same three patients were cultured with anti-CD3 to activate T-cells, along with control IgG or anti-PD-1 antibody (Nivolumab). If nuclear PD-L2 in DCs influenced the T-cells responses, then patients with more nuclear PD-L2+ DCs would have poor cytokine responses and PD-1 blockade would not improve the cytokine response. In contrast, patients with fewer DCs having nuclear PD-L2 (i.e., with PD-L2 on the cell surface), would be better at supporting T-cell functions and PD-1 blockade would therefore improve the responses.

After 72 hours of culture, patient D8 with the lowest numbers of DCs with nuclear PD-L2 in $10^7$ PBMCs (FIG. 8A), secreted the highest levels of TNF (FIG. 8B), IFN-γ (FIG. 8C) and IL-1β (FIG. 8D). In contrast, patient D6 had the highest number of DCs with nuclear PD-L2 in $10^7$ PBMCs (FIG. 8A) and was observed to secrete the lowest levels of TNF (FIG. 8B); IFN-γ (FIG. 8C) and IL-1β (FIG. 8D) after 72 hours of culture. IL-1β is secreted by DCs and induces the DCs to produce IL-12 when given CD40L signals for T-cells, setting up a positive loop to enhance immune responses. Patient D9 had an intermediate level of DCs with nuclear PD-L2 in $10^7$ PBMCs (FIG. 8A) and was observed to secrete intermediate to low levels of TNF (FIG. 8B), IFN-γ (FIG. 8C) and IL-1β (FIG. 8D) after 72 hours of culture.

Similarly, when PMBCs for the same three patients were cultured with anti-PD-1 antibody (Nivolumab), PBMCs from patient D8 (i.e., low nuclear PD-L2) responded with increased secretion of TNF (FIG. 8B), IFN-γ (FIG. 8C) and IL-1β (FIG. 8D) after 72 hours of culture. In contrast, patient D6 (i.e., highest nuclear PD-L2), showed no improvement in secretion of TNF (FIG. 8B); IFN-γ (FIG. 8C) or IL-1β (FIG. 8D). These data confirmed that nuclear PD-L2 was associated with poor responses to checkpoint inhibitor (e.g., PD-1) blockade. Of note, patient D9 had an intermediate level of nuclear PD-L2 and PD-1 blockade did not increase TNF (FIG. 8B) or IFN-γ (FIG. 8C) secretion after 72 hours. However, IL-1β levels were increased after 72 hours before dropping by 120 hours (FIGS. 8D and E). This is in stark contrast to the effect observed for patient D8 where levels continued to increase by 120 hours.

This result clearly indicates that nuclear PD-L2 in DCs influences IL-1β secretion by DCs, thereby preventing a positive loop to enhance immune responses. Importantly, subjects with intermediate nuclear PD-L2 (e.g., patient D9) had a limited response where there was an initial response to checkpoint inhibitor (i.e., PD-1) blockade with increased IL-1β secretion within 72 hours, but not after 120 hours. Taken together, these data demonstrate that an increase in accumulation of nuclear PD-L2 in DCs results in a substantial decline in immune responses. This decline is explained at least in part by a reduced secretion of IL-1β by DCs. Furthermore, these data show DCs with nuclear PD-L2 are no longer capable of stimulating T-cells to secrete IFN-γ, in addition to an overall loss of TNF secretion.

Taken together, these data demonstrate that an increase in accumulation of nuclear PD-L2 in DCs results in a substantial decline in immune responses. This decline is explained at least in part by a reduced secretion of IL-1β by DCs. Furthermore, these data show DCs with nuclear PD-L2 are no longer capable of stimulating T-cells to secrete IFN-γ, in addition to an overall loss of TNF secretion.

Figure 9:
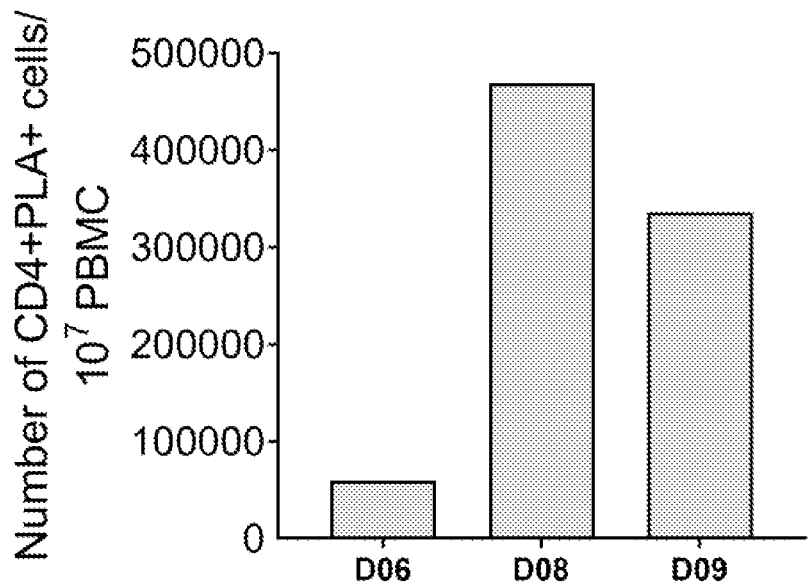
FIG. 9 is a graphical representation showing the association between number of CD4+ T-cells with nuclear PD-L2 measured by PLA in PBMCs from melanoma patients and number of CD4+FoxP3+Tbet+ regulatory T-cells. Proximity ligase assay was applied to PBMCs from three melanoma patients to measure PD-L2 which was in close proximity to histone H2A to confirm nuclear localization. (A) Number of CD3+CD4+ T-cells which were PLA+ (PD-L2+H2A+) in 10 million PBMCs. (B) Association between number of CD4+ T-cells with nuclear PD-L2 and number of CD4+FoxP3+ Tbet+ regulatory T-cells.
Figure 9:
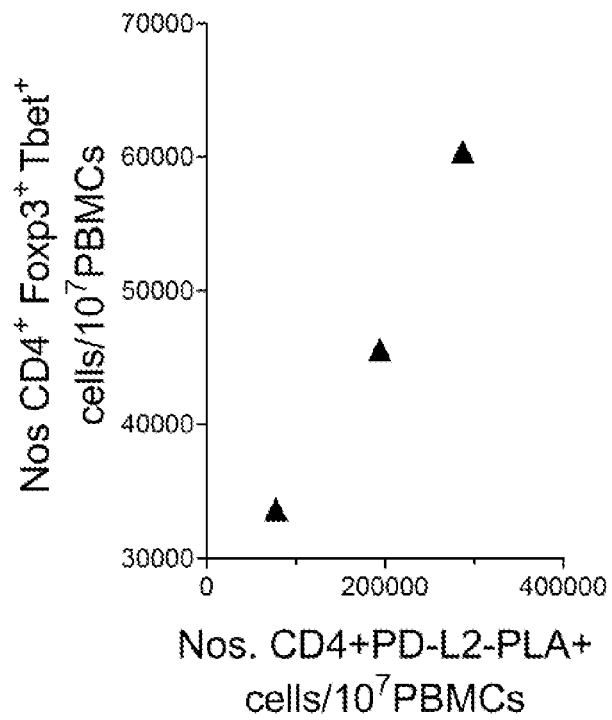

As for DCs, FIG. 9 shows the numbers of CD4+ T-cells with nuclear PD-L2 in $10^7$ PBMCs for three melanoma patients. These cells were also labelled to quantify CD4+ FoxP3+Tbet+ regulatory T-cells. There is a direct association between the number of CD4+ T-cells and number of this specific regulatory cell subpopulation. Taken together, these data suggest that after CD4+ T-cells express nuclear PD-L2, their phenotype changes to that of a regulatory T-cell with immune response dampening properties[23].

Figure 10:
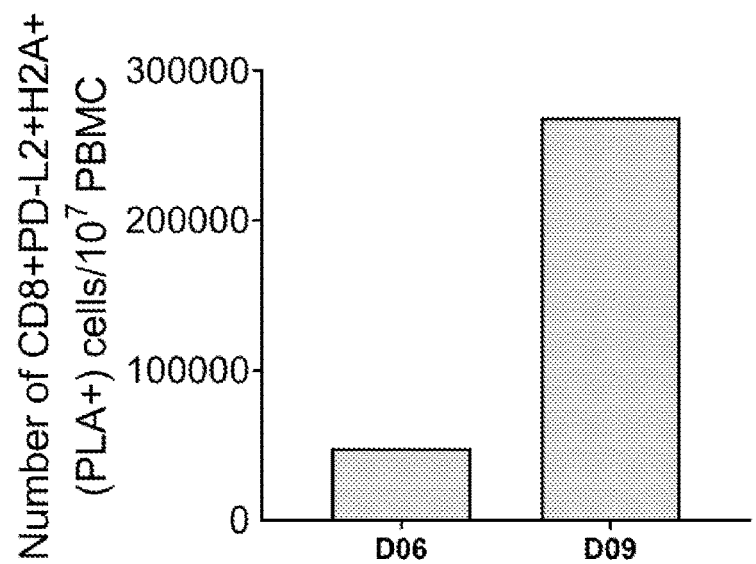
FIG. 10 is a graphical representation showing an association between number of CD8+ T-cells with nuclear PD-L2 measured by PLA in PBMCs from melanoma patients and number of CD+FoxP3+ regulatory T-cells. Proximity ligase assay was applied to PBMCs from three melanoma patients to measure PD-L2 which was in close proximity to histone H2A to confirm nuclear localization. (A) Number of CD3+CD8$^+$ T-cells which were PLA+ (PD-L2+H2A+) in 10 million PBMCs. (B) Association between number of CD8$^+$ T-cells with nuclear PD-L2 and number of CD8+FoxP3+ regulatory T-cells.
Figure 10:
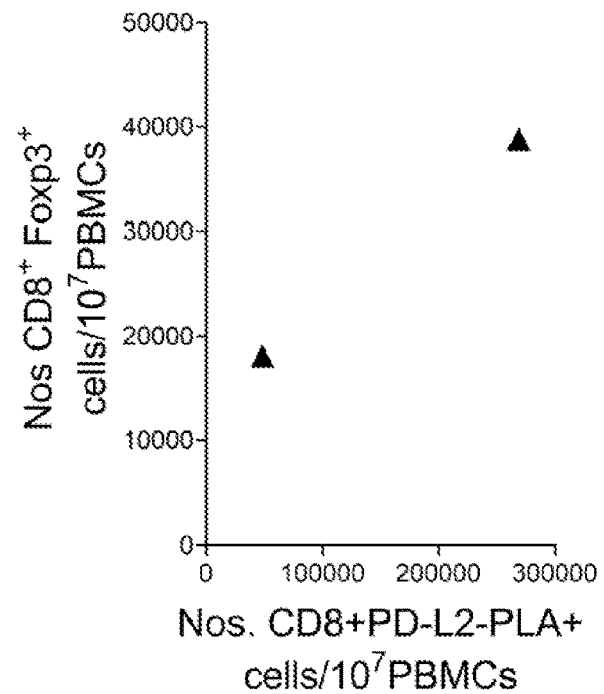

As for DCs, FIG. 10 shows the numbers of CD8+ T-cells with nuclear PD-L2 in $10^7$ PBMCs for three melanoma patients. These cells were also labelled to quantify CD8+ FoxP3+ regulatory T-cells. There is a direct association between the number of CD8+ T-cells and number of CD8+ regulatory cells. Taken together, these data suggest that after CD8+ T-cells express nuclear PD-L2, their phenotype changes to that of a regulatory T-cell with immune response dampening properties[24].

Materials & Methods

Reagent Preparation

Duolink® Wash Buffer and 1× PBS should be made prior to beginning the assay by dissolving the contents of one pouch in high purity water to a final volume of 1000 mL. Store 1× PBS at room temperature. Wash buffer may be stored at room temperature for short term storage (less than two weeks) or at 4° C. for long term storage. NOTE: Bring the solutions to room temperature before use.

Many Duolink® PLA reagents are supplied as concentrated stocks and are to be diluted immediately prior to use. Do not store diluted Duolink® PLA reagents.

Duolink® PLA Protocol

Before starting, suspended cell samples should be pre-treated with respect to fixation and permeabilization. Cells can be fixed, permeabilized, and blocked in bulk solution, and then aliquoted into tubes or wells for Duolink® PLA staining unless unique conditions for these steps are being scouted.

NOTE: Duolink® Blocking Solution and Antibody Diluent are provided with the Duolink® PLA Probes. If alternative solutions have been optimized for primary antibody performance by traditional flow cytometry, it is likely these can be used instead.

Blocking

After fixation and permeabilization, centrifuge and remove wash buffer from cells.

Use 10 µL of Duolink® Blocking Solution per µL volume of cell pellet (1 drop is ~30 µL).

Incubate in a 37° C. incubator for 60 minutes.

Primary Antibody Incubation

Dilute the primary antibody or antibodies to suitable concentration in the Duolink® Antibody Diluent or appropriate antibody diluent. Aliquot 100,000 cells per well of a U-bottom or V-bottom plate. Centrifuge the plate at 400×g for 5 minutes and remove the Duolink® Blocking Solution from the cells Add the primary antibody solution to each sample and mix well.

Incubate the plate, using the optimal incubation temperature and time for your primary antibodies.

Duolink® PLA Probe Incubation

Dilute the PLUS and MINUS PLA probes 1:5 in the Duolink® Antibody Diluent. For a 100 µL reaction, take 20 µL of PLA probe MINUS stock, 20 µL of PLA probe PLUS stock and 60 µL of Antibody Diluent. Make sufficient solution for all samples.

Centrifuge at 400×g for 5 minutes and remove the solution from the cells.

Wash the cells twice with 200 μL of Duolink® Wash Buffer per well, centrifuge at 400×g for 5 minutes, and remove the solution from the cells.

Add the PLA probe solution and mix well.

Incubate in a 37° C. incubator for 1 hour.

Ligation

NOTE: Wait to add the ligase until immediately prior to addition to the sample. Make sure ligation buffer is completely thawed and mixed well prior to usage.

Vortex the 5× Duolink® Ligation buffer.

Dilute the 5× Ligation buffer 1:5 in high purity water and mix. For a 100 μL reaction, add 20 μL of the 5× Ligation buffer to 77.5 μL of high purity water. Make sufficient solution for all samples.

Centrifuge at 400×g for 5 minutes and remove the solution from the cells.

Wash the cells twice with 200 μL of Duolink® Wash Buffer per well, centrifuge at 400×g for 5 minutes, and remove the solution from the cells.

During the wash, retrieve the Ligase from the freezer using a freezer block (−20° C.).

Add Ligase to the 1× Ligation buffer at a 1:40 dilution and mix. For 100 μL ligation solution, add 2.5 μL of Ligase to 97.5 μL of the 1× ligation buffer.

Add the ligation solution and mix well.

Incubate in a 37° C. incubator for 30 minutes.

Amplification

NOTE: Wait to add the polymerase until immediately prior to addition to the sample.

Vortex the 5× Duolink® Amplification buffer.

Dilute the 5× Amplification buffer 1:5 in high purity water and mix. For 100 μL reaction, add 20 μL of the 5× Amplification buffer to 78.75 μL of high purity water. Make sufficient solution for all samples.

Centrifuge at 400×g for 5 minutes and remove the solution from the cells.

Wash the cells twice with 200 μL of Duolink® Wash Buffer per well, centrifuge at 400×g for 5 minutes, and remove the solution from the cells.

During the wash, retrieve the Polymerase from the freezer using a freezer block (−20° C.).

Add Polymerase to the 1× Amplification buffer at a 1:80 dilution and mix. For 100 μL amplification solution, add 1.25 μL of Polymerase to 98.75 μL of the 1× amplification buffer Add the amplification solution and mix well. Incubate in a 37° C. incubator for 100 minutes. NOTE: Longer amplification time (up to overnight) may be required for low abundance proteins or protein interactions.

Detection

NOTE: The Duolink® Detection Buffer is light-sensitive. Protect from light.

Vortex the 5× Detection Buffer.

Dilute 1:5 in high purity water and mix. For 100 μL reaction, add 20 μL of the 5× Detection buffer to 80 μL of high purity water. Make sufficient solution for all samples.

Centrifuge at 400×g for 5 minutes and remove the solution from the cells.

Wash the cells twice with 200 μL of Duolink® Wash Buffer per well, centrifuge at 400×g for 5 minutes, and remove the solution from the cells.

Add the detection solution and mix well.

Incubate in a 37° C. incubator for 30 minutes.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the disclosure without limiting the disclosure to any one embodiment or specific collection of features. Those of skill in the art will therefore appreciate that, in light of the instant disclosure, various modifications and changes can be made in the particular embodiments exemplified without departing from the scope of the present disclosure. All such modifications and changes are intended to be included within the scope of the appended claims.

BIBLIOGRAPHY

1. Latchman, Y. et al. PD-L2 is a second ligand for PD-1 and inhibits T-cell activation. *Nat Immunol* 2, 261-268 (2001).
2. Brown, J. A. et al. Blockade of programmed death-1 ligands on dendritic cells enhances T-cell activation and cytokine production. *J Immunol* 170, 1257-1266 (2003).
3. Cai, G. et al. PD-1 ligands, negative regulators for activation of naive, memory, and recently activated human CD4+ T cells. *Cell Immunol* 230, 89-98, doi: 10.1016/j.cellimm.2004.09.004 (2004).
4. Xiao, Y. et al. RGMb is a novel binding partner for PD-L2 and its engagement with PD-L2 promotes respiratory tolerance. *J Exp Med* 211, 943-959, doi:10.1084/jem.20130790 (2014).
5. Liu, X. et al. B7DC/PDL2 promotes tumor immunity by a PD-1-independent mechanism. *J Exp Med* 197, 1721-1730, doi:10.1084/jem.20022089 jem.20022089 [pii] (2003).
6. Shin, T. et al. Cooperative B7-1/2 (CD80/CD86) and B7-DC costimulation of CD4+ T cells independent of the PD-1 receptor. *J Exp Med* 198, 31-38, doi:10.1084/jem.20030242 (2003).
7. Karunarathne, D. S. et al. Programmed Death-1 Ligand 2-Mediated Regulation of the PD-L1 to PD-1 Axis Is Essential for Establishing CD4(+) T Cell Immunity. *Immunity* 45, 333-345, doi:10.1016/j.immuni.2016.07.017 (2016).
8. Kuipers, H. et al. Contribution of the PD-1 ligands/PD-1 signaling pathway to dendritic cell-mediated CD4+ T cell activation. *Eur J Immunol* 36, 2472-2482, doi:10.1002/eji.200635978 (2006).
9. Wykes, M. N. & Lewin, S. R. Immune checkpoint blockade in infectious diseases. *Nature Reviews Immunology*, doi:10.1038/nri.2017.112 (2017).
10. Wykes, M. N., Liu, X. Q., Jiang, S., Hirunpetcharat, C. & Good, M. F. Systemic tumor necrosis factor generated during lethal *Plasmodium* infections impairs dendritic cell function. *J Immunol* 179, 3982-3987 (2007).
11. Wykes, M. N. et al. *Plasmodium* Strain Determines Dendritic Cell Function Essential for Survival from Malaria. *PLoS Pathog* 3, e96 (2007).
12. Liang, S. C. et al. PD-L1 and PD-L2 have distinct roles in regulating host immunity to cutaneous leishmaniasis. *Eur J Immunol* 36, 58-64 (2006).
13. Zhou, Q. et al. Coexpression of Tim-3 and PD-1 identifies a CD8+ T-cell exhaustion phenotype in mice with disseminated acute myelogenous leukemia. *Blood* 117, 4501-4510, doi:10.1182/blood-2010-10-310425 (2011).
14. Ngiow, S. F. et al. A Threshold Level of Intratumor CD8+ T-cell PD1 Expression Dictates Therapeutic Response to Anti-PD1. *Cancer Res* 75, 3800-3811, doi: 10.1158/0008-5472.CAN-15-1082 (2015).

15. Yearley, J. H. et al. PD-L2 Expression in Human Tumors: Relevance to Anti-PD-1 Therapy in Cancer. *Clin Cancer Res* 23, 3158-3167, doi:10.1158/1078-0432.CCR-16-1761 (2017).
16. Topalian, S. L. et al. Safety, activity, and immune correlates of anti-PD-1 antibody in cancer. *N Engl J Med* 366, 2443-2454, doi:10.1056/NEJMoa1200690 (2012).
17. Patel, S. P. & Kurzrock, R. PD-L1 Expression as a Predictive Biomarker in Cancer Immunotherapy. *Mol Cancer Ther* 14, 847-856, doi:10.1158/1535-7163.MCT-14-0983 (2015).
18. Friedman, C. F. & Postow, M. A. Emerging Tissue and Blood-Based Biomarkers that may Predict Response to Immune Checkpoint Inhibition. *Current oncology reports* 18, 21, doi:10.1007/s11912-016-0509-x (2016).
19. Tseng, S. Y. et al. B7-DC, a new dendritic cell molecule with potent costimulatory properties for T cells. *J Exp Med* 193, 839-846 (2001).
20. Shin, T. et al. In vivo costimulatory role of B7-DC in tuning T helper cell 1 and cytotoxic T lymphocyte responses. *J Exp Med* 201, 1531-1541, doi:jem.20050072 [pii]10.1084/jem.20050072 (2005).
21. Ammannagari, N. & Atasoy, A. Current status of immunotherapy and immune biomarkers in gastro-esophageal cancers. *Journal of gastrointestinal oncology* 9, 196-207, doi:10.21037/jgo.2017.06.12 (2018).
22. Forster, M. D. & Devlin, M. J. Immune Checkpoint Inhibition in Head and Neck Cancer. *Frontiers in oncology* 8, 310, doi:10.3389/fonc.2018.00310 (2018).
23. Phares, T. W., et al., *A Peptide-Based PD1 Antagonist Enhances T-Cell Priming and Efficacy of a Prophylactic Malaria Vaccine and Promotes Survival in a Lethal Malaria Model*. Frontiers in Immunology, 2020. 11(1377).
24. Robb, R. J., et al., *Identification and expansion of highly suppressive CD8(+)FoxP3(+) regulatory T cells after experimental allogeneic bone marrow transplantation*. Blood, 2012. 119(24): p. 5898-908.

What is claimed is:

1. A complex comprising programmed cell death ligand 2 (PD-L2) and a nuclear binding partner of PD-L2, a first antibody that is bound specifically to PD-L2 of the complex and a second antibody bound to the nuclear binding partner of the complex, wherein the nuclear binding partner of PD-L2 is selected from the group consisting of an H2A polypeptide, an H2AX polypeptide and an H4 polypeptide.

2. The complex of claim 1, wherein the complex is located in a cell or lysate thereof.

3. The complex of claim 2, wherein the cell is selected from the group consisting of an antigen-presenting cell, an immune effector cell and a tumor cell.

4. The complex of claim 3, wherein the antigen-presenting cell is a dendritic cell.

5. The complex of claim 3, wherein the immune effector cell is a B-cell or T-cell.

6. The complex of claim 1, further comprising a third antibody that binds to each of the first and second antibodies of the complex.

7. The complex of claim 6, wherein the third antibody is detectably labeled.

8. A cell or lysate thereof, comprising a complex comprising PD-L2 and a nuclear binding partner of PD-L2, a first antibody that is bound specifically to PD-L2 of the complex and a second antibody bound to the nuclear binding partner of the complex, wherein the nuclear binding partner of PD-L2 is selected from the group consisting of an H2A polypeptide, an H2AX polypeptide and an H4 polypeptide.

9. The cell or lysate of claim 8, wherein the cell is selected from the group consisting of an antigen-presenting cell, an immune effector cell and a tumor cell.

10. The cell or lysate of claim 9, wherein the antigen-presenting cell is a dendritic cell.

11. The cell or lysate of claim 9, wherein the immune effector cell is a B-cell or T-cell.

* * * * *